US008262680B2

(12) United States Patent
Swain et al.

(10) Patent No.: US 8,262,680 B2
(45) Date of Patent: Sep. 11, 2012

(54) ANASTOMOTIC DEVICE

(75) Inventors: Christopher P. Swain, London (GB); Priya Jamidar, Gullford, CT (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 628 days.

(21) Appl. No.: 12/045,318

(22) Filed: Mar. 10, 2008

(65) Prior Publication Data
US 2009/0227828 A1    Sep. 10, 2009

(51) Int. Cl.
*A61B 17/08* (2006.01)
(52) U.S. Cl. .......................... 606/151; 606/215
(58) Field of Classification Search .................. 606/139, 606/151, 153–158, 215–216; 623/1.23; 128/898
See application file for complete search history.

(56) References Cited

U.S. PATENT DOCUMENTS

| | | |
|---|---|---|
| 645,576 A | 3/1900 | Telsa |
| 649,621 A | 5/1900 | Tesla |
| 787,412 A | 4/1905 | Tesla |
| 1,127,948 A | 2/1915 | Wappler |
| 1,482,653 A | 2/1924 | Lilly |
| 1,625,602 A | 4/1927 | Gould et al. |
| 2,028,635 A | 1/1936 | Wappler |
| 2,031,682 A | 2/1936 | Wappler et al. |
| 2,113,246 A | 4/1938 | Wappler |
| 2,155,365 A | 4/1939 | Rankin |
| 2,191,858 A | 2/1940 | Moore |
| 2,196,620 A | 4/1940 | Attarian |
| 2,388,137 A | 10/1945 | Graumlich |
| 2,493,108 A | 1/1950 | Casey, Jr. |
| 2,504,152 A | 4/1950 | Riker et al. |
| 2,938,382 A | 5/1960 | De Graaf |
| 2,952,206 A | 9/1960 | Becksted |
| 3,069,195 A | 12/1962 | Buck |
| 3,170,471 A | 2/1965 | Schnitzer |
| 3,435,824 A | 4/1969 | Gamponia |
| 3,470,876 A | 10/1969 | Barchilon |
| 3,595,239 A | 7/1971 | Petersen |
| 3,669,487 A | 6/1972 | Roberts et al. |

(Continued)

FOREIGN PATENT DOCUMENTS
AU           666310 B2    2/1996
(Continued)

OTHER PUBLICATIONS

U.S. Appl. No. 11/706,591, filed Feb. 15, 2007.
(Continued)

*Primary Examiner* — Corrine M McDermott
*Assistant Examiner* — Todd J Scherbel

(57) ABSTRACT

An apparatus and system for forming a compression anastomosis. The apparatus includes an anastomotic device with an anastomotic portion including a first end and a second end. The anastomotic portion is formed of a ferrous, magnetic, or paramagnetic material. At least one flexible portion protrudes from the first end of the anastomotic portion. The at least one flexible portion includes an articulation node located at a predetermined distance from the first end of the anastomotic portion. The articulation node enables the at least one flexible portion to move relative to the anastomotic portion. The system further includes a magnet having a first end and a second end. The magnet is adapted to magnetically couple to the anastomotic portion of the anastomotic device and to compress tissue between the magnet and the anastomotic device. The compressive force on the tissue is sufficient to create a compression anastomosis through the tissue.

23 Claims, 11 Drawing Sheets

U.S. PATENT DOCUMENTS

| | | |
|---|---|---|
| 3,746,881 A | 7/1973 | Fitch et al. |
| 3,799,672 A | 3/1974 | Vurek |
| 3,854,473 A | 12/1974 | Matsuo |
| 3,946,740 A | 3/1976 | Bassett |
| 3,948,251 A | 4/1976 | Hosono |
| 3,994,301 A | 11/1976 | Agris |
| 4,011,872 A | 3/1977 | Komiya |
| 4,012,812 A | 3/1977 | Black |
| 4,085,743 A | 4/1978 | Yoon |
| 4,164,225 A | 8/1979 | Johnson et al. |
| 4,178,920 A | 12/1979 | Cawood, Jr. et al. |
| 4,207,873 A | 6/1980 | Kruy |
| 4,235,238 A | 11/1980 | Ogiu et al. |
| 4,258,716 A | 3/1981 | Sutherland |
| 4,269,174 A | 5/1981 | Adair |
| 4,278,077 A | 7/1981 | Mizumoto |
| 4,285,344 A | 8/1981 | Marshall |
| 4,311,143 A | 1/1982 | Komiya |
| 4,329,980 A | 5/1982 | Terada |
| 4,396,021 A | 8/1983 | Baumgartner |
| 4,406,656 A | 9/1983 | Hattler et al. |
| 4,452,246 A | 6/1984 | Bader et al. |
| 4,461,281 A | 7/1984 | Carson |
| 4,491,132 A | 1/1985 | Aikins |
| 4,527,331 A | 7/1985 | Lasner et al. |
| 4,527,564 A | 7/1985 | Eguchi et al. |
| 4,538,594 A | 9/1985 | Boebel et al. |
| D281,104 S | 10/1985 | Davison |
| 4,569,347 A | 2/1986 | Frisbie |
| 4,580,551 A | 4/1986 | Siegmund et al. |
| 4,646,722 A | 3/1987 | Silverstein et al. |
| 4,653,476 A | 3/1987 | Bonnet |
| 4,655,219 A | 4/1987 | Petruzzi |
| 4,669,470 A | 6/1987 | Brandfield |
| 4,671,477 A | 6/1987 | Cullen |
| 4,685,447 A | 8/1987 | Iversen et al. |
| 4,711,240 A | 12/1987 | Goldwasser et al. |
| 4,712,545 A | 12/1987 | Honkanen |
| 4,721,116 A | 1/1988 | Schintgen et al. |
| 4,733,662 A | 3/1988 | DeSatnick et al. |
| D295,894 S | 5/1988 | Sharkany et al. |
| 4,763,669 A | 8/1988 | Jaeger |
| 4,770,188 A | 9/1988 | Chikama |
| 4,815,450 A | 3/1989 | Patel |
| 4,823,794 A | 4/1989 | Pierce |
| 4,829,999 A | 5/1989 | Auth |
| 4,867,140 A | 9/1989 | Hovis et al. |
| 4,873,979 A | 10/1989 | Hanna |
| 4,880,015 A | 11/1989 | Nierman |
| 4,911,148 A | 3/1990 | Sosnowski et al. |
| 4,926,860 A | 5/1990 | Stice et al. |
| 4,938,214 A | 7/1990 | Specht et al. |
| 4,950,273 A | 8/1990 | Briggs |
| 4,950,285 A | 8/1990 | Wilk |
| 4,960,133 A | 10/1990 | Hewson |
| 4,977,887 A | 12/1990 | Gouda |
| 4,979,950 A * | 12/1990 | Transue et al. ............ 606/158 |
| 4,984,581 A | 1/1991 | Stice |
| 5,007,917 A | 4/1991 | Evans |
| 5,010,876 A | 4/1991 | Henley et al. |
| 5,020,514 A | 6/1991 | Heckele |
| 5,020,535 A | 6/1991 | Parker et al. |
| 5,025,778 A | 6/1991 | Silverstein et al. |
| 5,033,169 A | 7/1991 | Bindon |
| 5,037,433 A | 8/1991 | Wilk et al. |
| 5,041,129 A | 8/1991 | Hayhurst et al. |
| 5,046,513 A | 9/1991 | Gatturna et al. |
| 5,050,585 A | 9/1991 | Takahashi |
| 5,052,372 A | 10/1991 | Shapiro |
| 5,065,516 A | 11/1991 | Dulebohn |
| 5,066,295 A | 11/1991 | Kozak et al. |
| 5,123,913 A | 6/1992 | Wilk et al. |
| 5,123,914 A | 6/1992 | Cope |
| 5,133,727 A | 7/1992 | Bales et al. |
| 5,147,374 A | 9/1992 | Fernandez |
| 5,174,300 A | 12/1992 | Bales et al. |
| 5,176,126 A | 1/1993 | Chikama |
| 5,190,050 A | 3/1993 | Nitzsche |
| 5,190,555 A | 3/1993 | Wetter et al. |
| 5,192,284 A | 3/1993 | Pleatman |
| 5,201,752 A | 4/1993 | Brown et al. |
| 5,201,908 A | 4/1993 | Jones |
| 5,203,785 A | 4/1993 | Slater |
| 5,203,787 A | 4/1993 | Noblitt et al. |
| 5,209,747 A | 5/1993 | Knoepfler |
| 5,217,003 A | 6/1993 | Wilk |
| 5,217,453 A | 6/1993 | Wilk |
| 5,219,357 A | 6/1993 | Honkanen et al. |
| 5,219,358 A | 6/1993 | Bendel et al. |
| 5,222,362 A | 6/1993 | Maus et al. |
| 5,222,965 A | 6/1993 | Haughton |
| 5,234,437 A | 8/1993 | Sepetka |
| 5,234,453 A | 8/1993 | Smith et al. |
| 5,235,964 A | 8/1993 | Abenaim |
| 5,242,456 A | 9/1993 | Nash et al. |
| 5,246,424 A | 9/1993 | Wilk |
| 5,259,366 A | 11/1993 | Reydel et al. |
| 5,263,958 A | 11/1993 | deGuillebon et al. |
| 5,273,524 A | 12/1993 | Fox et al. |
| 5,275,607 A | 1/1994 | Lo et al. |
| 5,284,128 A | 2/1994 | Hart |
| 5,284,162 A | 2/1994 | Wilk |
| 5,287,845 A | 2/1994 | Faul et al. |
| 5,290,299 A | 3/1994 | Fain et al. |
| 5,290,302 A | 3/1994 | Pericic |
| 5,295,977 A | 3/1994 | Cohen et al. |
| 5,297,536 A | 3/1994 | Wilk |
| 5,301,061 A | 4/1994 | Nakada et al. |
| 5,312,333 A | 5/1994 | Churinetz et al. |
| 5,312,351 A | 5/1994 | Gerrone |
| 5,312,416 A | 5/1994 | Spaeth et al. |
| 5,312,423 A | 5/1994 | Rosenbluth et al. |
| 5,318,589 A | 6/1994 | Lichtman |
| 5,320,636 A | 6/1994 | Slater |
| 5,325,845 A | 7/1994 | Adair |
| 5,330,471 A | 7/1994 | Eggers |
| 5,330,486 A * | 7/1994 | Wilk ............................ 606/139 |
| 5,330,488 A | 7/1994 | Goldrath |
| 5,330,496 A | 7/1994 | Alferness |
| 5,330,502 A | 7/1994 | Hassler et al. |
| 5,331,971 A | 7/1994 | Bales et al. |
| 5,334,198 A | 8/1994 | Hart et al. |
| 5,344,428 A | 9/1994 | Griffiths |
| 5,350,391 A | 9/1994 | Iacovelli |
| 5,352,184 A | 10/1994 | Goldberg et al. |
| 5,352,222 A | 10/1994 | Rydell |
| 5,354,302 A | 10/1994 | Ko |
| 5,354,311 A | 10/1994 | Kambin et al. |
| 5,356,408 A | 10/1994 | Rydell |
| 5,364,408 A | 11/1994 | Gordon |
| 5,364,410 A | 11/1994 | Failla et al. |
| 5,366,466 A | 11/1994 | Christian et al. |
| 5,366,467 A | 11/1994 | Lynch et al. |
| 5,368,605 A | 11/1994 | Miller, Jr. |
| 5,370,647 A | 12/1994 | Graber et al. |
| 5,370,679 A | 12/1994 | Atlee, III |
| 5,374,273 A | 12/1994 | Nakao et al. |
| 5,374,275 A | 12/1994 | Bradley et al. |
| 5,374,277 A | 12/1994 | Hassler |
| 5,377,695 A | 1/1995 | An Haack |
| 5,383,877 A | 1/1995 | Clarke |
| 5,383,888 A | 1/1995 | Zvenyatsky et al. |
| 5,386,817 A | 2/1995 | Jones |
| 5,391,174 A | 2/1995 | Weston |
| 5,392,789 A | 2/1995 | Slater et al. |
| 5,395,386 A | 3/1995 | Slater |
| 5,401,248 A | 3/1995 | Bencini |
| 5,403,328 A | 4/1995 | Shallman |
| 5,403,342 A | 4/1995 | Tovey et al. |
| 5,403,348 A | 4/1995 | Bonutti |
| 5,405,073 A | 4/1995 | Porter |
| 5,405,359 A | 4/1995 | Pierce |
| 5,409,478 A | 4/1995 | Gerry et al. |
| 5,417,699 A | 5/1995 | Klein et al. |
| 5,423,821 A | 6/1995 | Pasque |
| 5,433,721 A | 7/1995 | Hooven et al. |
| 5,439,471 A | 8/1995 | Kerr |

| | | |
|---|---|---|
| 5,439,478 A | 8/1995 | Palmer |
| 5,441,059 A | 8/1995 | Dannan |
| 5,441,499 A | 8/1995 | Fritzsch |
| 5,443,463 A | 8/1995 | Stern et al. |
| 5,445,638 A | 8/1995 | Rydell et al. |
| 5,449,021 A | 9/1995 | Chikama |
| 5,456,667 A | 10/1995 | Ham et al. |
| 5,456,684 A | 10/1995 | Schmidt et al. |
| 5,458,131 A | 10/1995 | Wilk |
| 5,458,583 A | 10/1995 | McNeely et al. |
| 5,460,168 A | 10/1995 | Masubuchi et al. |
| 5,460,629 A | 10/1995 | Shlain et al. |
| 5,462,561 A | 10/1995 | Voda |
| 5,465,731 A | 11/1995 | Bell et al. |
| 5,467,763 A | 11/1995 | McMahon et al. |
| 5,468,250 A | 11/1995 | Paraschac et al. |
| 5,470,308 A | 11/1995 | Edwards et al. |
| 5,470,320 A | 11/1995 | Tiefenbrun et al. |
| 5,478,347 A | 12/1995 | Aranyi |
| 5,480,404 A | 1/1996 | Kammerer et al. |
| 5,482,054 A | 1/1996 | Slater et al. |
| 5,484,451 A | 1/1996 | Akopov et al. |
| 5,489,256 A | 2/1996 | Adair |
| 5,496,347 A | 3/1996 | Hashiguchi et al. |
| 5,499,990 A | 3/1996 | Schulken et al. |
| 5,499,992 A | 3/1996 | Meade et al. |
| 5,501,692 A | 3/1996 | Riza |
| 5,503,616 A | 4/1996 | Jones |
| 5,505,686 A | 4/1996 | Willis et al. |
| 5,507,755 A | 4/1996 | Gresl et al. |
| 5,511,564 A | 4/1996 | Wilk |
| 5,514,157 A | 5/1996 | Nicholas et al. |
| 5,522,829 A | 6/1996 | Michalos |
| 5,522,830 A | 6/1996 | Aranyi |
| 5,527,321 A | 6/1996 | Hinchliffe |
| 5,536,248 A | 7/1996 | Weaver et al. |
| 5,540,648 A | 7/1996 | Yoon |
| 5,554,151 A | 9/1996 | Hinchliffe |
| 5,555,883 A | 9/1996 | Avitall |
| 5,558,133 A | 9/1996 | Bortoli et al. |
| 5,562,693 A | 10/1996 | Devlin et al. |
| 5,569,243 A | 10/1996 | Kortenbach et al. |
| 5,569,298 A | 10/1996 | Schnell |
| 5,573,540 A | 11/1996 | Yoon |
| 5,578,030 A | 11/1996 | Levin |
| 5,582,611 A | 12/1996 | Tsuruta et al. |
| 5,582,617 A | 12/1996 | Klieman et al. |
| 5,584,845 A | 12/1996 | Hart |
| 5,591,179 A | 1/1997 | Edelstein |
| 5,593,420 A | 1/1997 | Eubanks, Jr. et al. |
| 5,595,562 A | 1/1997 | Grier |
| 5,597,378 A | 1/1997 | Jervis |
| 5,601,573 A | 2/1997 | Fogelberg et al. |
| 5,601,588 A | 2/1997 | Tonomura et al. |
| 5,604,531 A | 2/1997 | Iddan et al. |
| 5,607,389 A | 3/1997 | Edwards et al. |
| 5,607,450 A | 3/1997 | Zvenyatsky et al. |
| 5,613,975 A | 3/1997 | Christy |
| 5,618,303 A | 4/1997 | Marlow et al. |
| 5,620,415 A | 4/1997 | Lucey et al. |
| 5,624,399 A | 4/1997 | Ackerman |
| 5,624,431 A | 4/1997 | Gerry et al. |
| 5,626,578 A | 5/1997 | Tihon |
| 5,628,732 A | 5/1997 | Antoon, Jr. et al. |
| 5,630,782 A | 5/1997 | Adair |
| 5,643,283 A | 7/1997 | Younker |
| 5,643,292 A | 7/1997 | Hart |
| 5,643,294 A | 7/1997 | Tovey et al. |
| 5,644,798 A | 7/1997 | Shah |
| 5,645,083 A | 7/1997 | Essig et al. |
| 5,645,565 A | 7/1997 | Rudd et al. |
| 5,649,372 A | 7/1997 | Souza |
| 5,653,677 A | 8/1997 | Okada et al. |
| 5,653,690 A | 8/1997 | Booth et al. |
| 5,653,722 A | 8/1997 | Kieturakis |
| 5,662,663 A | 9/1997 | Shallman |
| 5,669,875 A | 9/1997 | van Eerdenburg |
| 5,681,324 A | 10/1997 | Kammerer et al. |
| 5,681,330 A | 10/1997 | Hughett et al. |
| 5,685,820 A | 11/1997 | Riek et al. |
| 5,690,656 A * | 11/1997 | Cope et al. .................... 606/153 |
| 5,690,660 A | 11/1997 | Kauker et al. |
| 5,695,448 A | 12/1997 | Kimura et al. |
| 5,695,505 A | 12/1997 | Yoon |
| 5,695,511 A | 12/1997 | Cano et al. |
| 5,700,275 A | 12/1997 | Bell et al. |
| 5,702,438 A | 12/1997 | Avitall |
| 5,704,892 A | 1/1998 | Adair |
| 5,709,708 A | 1/1998 | Thal |
| 5,716,326 A | 2/1998 | Dannan |
| 5,730,740 A | 3/1998 | Wales et al. |
| 5,735,849 A | 4/1998 | Baden et al. |
| 5,741,234 A | 4/1998 | Aboul-Hosn |
| 5,741,278 A | 4/1998 | Stevens |
| 5,741,285 A | 4/1998 | McBrayer et al. |
| 5,746,759 A | 5/1998 | Meade et al. |
| 5,749,881 A | 5/1998 | Sackier et al. |
| 5,749,889 A | 5/1998 | Bacich et al. |
| 5,752,951 A | 5/1998 | Yanik |
| 5,755,731 A | 5/1998 | Grinberg |
| 5,766,167 A | 6/1998 | Eggers et al. |
| 5,766,170 A | 6/1998 | Eggers |
| 5,766,205 A | 6/1998 | Zvenyatsky et al. |
| 5,769,849 A | 6/1998 | Eggers |
| 5,779,701 A | 7/1998 | McBrayer et al. |
| 5,779,716 A | 7/1998 | Cano et al. |
| 5,779,727 A | 7/1998 | Orejola |
| 5,782,859 A | 7/1998 | Nicholas et al. |
| 5,782,866 A | 7/1998 | Wenstrom, Jr. |
| 5,791,022 A | 8/1998 | Bohman |
| 5,792,113 A | 8/1998 | Kramer et al. |
| 5,792,153 A | 8/1998 | Swain et al. |
| 5,792,165 A | 8/1998 | Klieman et al. |
| 5,797,835 A | 8/1998 | Green |
| 5,797,928 A | 8/1998 | Kogasaka |
| 5,797,939 A | 8/1998 | Yoon |
| 5,797,941 A | 8/1998 | Schulze et al. |
| 5,803,903 A | 9/1998 | Athas et al. |
| 5,808,665 A | 9/1998 | Green |
| 5,810,806 A | 9/1998 | Ritchart et al. |
| 5,810,849 A | 9/1998 | Kontos |
| 5,810,865 A | 9/1998 | Koscher et al. |
| 5,810,876 A | 9/1998 | Kelleher |
| 5,810,877 A | 9/1998 | Roth et al. |
| 5,813,976 A | 9/1998 | Filipi et al. |
| 5,814,058 A | 9/1998 | Carlson et al. |
| 5,817,061 A | 10/1998 | Goodwin et al. |
| 5,817,107 A | 10/1998 | Schaller |
| 5,817,119 A | 10/1998 | Klieman et al. |
| 5,819,736 A | 10/1998 | Avny et al. |
| 5,824,071 A | 10/1998 | Nelson et al. |
| 5,827,281 A | 10/1998 | Levin |
| 5,827,299 A | 10/1998 | Thomason et al. |
| 5,830,231 A | 11/1998 | Geiges, Jr. |
| 5,833,700 A | 11/1998 | Fogelberg et al. |
| 5,833,703 A | 11/1998 | Manushakian |
| 5,843,017 A | 12/1998 | Yoon |
| 5,843,121 A | 12/1998 | Yoon |
| 5,849,022 A | 12/1998 | Sakashita et al. |
| 5,853,374 A | 12/1998 | Hart et al. |
| 5,855,585 A | 1/1999 | Kontos |
| 5,860,913 A | 1/1999 | Yamaya et al. |
| 5,860,995 A | 1/1999 | Berkelaar |
| 5,868,762 A | 2/1999 | Cragg et al. |
| 5,876,411 A | 3/1999 | Kontos |
| 5,882,331 A | 3/1999 | Sasaki |
| 5,882,344 A | 3/1999 | Stouder, Jr. |
| 5,893,846 A | 4/1999 | Bales et al. |
| 5,893,874 A | 4/1999 | Bourque et al. |
| 5,893,875 A | 4/1999 | O'Connor et al. |
| 5,899,919 A | 5/1999 | Eubanks, Jr. et al. |
| 5,902,254 A | 5/1999 | Magram |
| 5,904,702 A | 5/1999 | Ek et al. |
| 5,908,420 A | 6/1999 | Parins et al. |
| 5,911,737 A | 6/1999 | Lee et al. |
| 5,916,147 A | 6/1999 | Boury |
| 5,921,993 A | 7/1999 | Yoon |
| 5,921,997 A | 7/1999 | Fogelberg et al. |

| | | | | | | |
|---|---|---|---|---|---|---|
| 5,922,008 A | 7/1999 | Gimpelson | 6,258,064 B1 | 7/2001 | Smith et al. | |
| 5,925,052 A | 7/1999 | Simmons | 6,261,242 B1 | 7/2001 | Roberts et al. | |
| 5,928,255 A | 7/1999 | Meade et al. | 6,264,664 B1 | 7/2001 | Avellanet | |
| 5,928,266 A | 7/1999 | Kontos | 6,270,497 B1 | 8/2001 | Sekino et al. | |
| 5,936,536 A | 8/1999 | Morris | 6,270,505 B1 | 8/2001 | Yoshida et al. | |
| 5,944,718 A | 8/1999 | Austin et al. | 6,277,136 B1 | 8/2001 | Bonutti | |
| 5,951,549 A | 9/1999 | Richardson et al. | 6,283,963 B1 | 9/2001 | Regula | |
| 5,954,720 A | 9/1999 | Wilson et al. | 6,293,909 B1 | 9/2001 | Chu et al. | |
| 5,954,731 A | 9/1999 | Yoon | 6,293,952 B1 | 9/2001 | Brosens et al. | |
| 5,957,943 A | 9/1999 | Vaitekunas | 6,296,630 B1 | 10/2001 | Altman et al. | |
| 5,957,953 A | 9/1999 | DiPoto et al. | 6,322,578 B1 | 11/2001 | Houle et al. | |
| 5,971,995 A | 10/1999 | Rousseau | 6,326,177 B1 | 12/2001 | Schoenbach et al. | |
| 5,976,074 A | 11/1999 | Moriyama | 6,328,730 B1 | 12/2001 | Harkrider, Jr. | |
| 5,976,075 A | 11/1999 | Beane et al. | 6,350,267 B1 | 2/2002 | Stefanchik | |
| 5,976,130 A | 11/1999 | McBrayer et al. | 6,350,278 B1 | 2/2002 | Lenker et al. | |
| 5,976,131 A | 11/1999 | Guglielmi et al. | 6,352,503 B1 | 3/2002 | Matsui et al. | |
| 5,980,539 A | 11/1999 | Kontos | 6,352,543 B1 * | 3/2002 | Cole | 606/153 |
| 5,980,556 A | 11/1999 | Giordano et al. | 6,355,035 B1 | 3/2002 | Manushakian | |
| 5,984,938 A | 11/1999 | Yoon | 6,361,534 B1 | 3/2002 | Chen et al. | |
| 5,984,939 A | 11/1999 | Yoon | 6,371,956 B1 | 4/2002 | Wilson et al. | |
| 5,989,182 A | 11/1999 | Hori et al. | 6,379,366 B1 | 4/2002 | Fleischman et al. | |
| 5,993,447 A | 11/1999 | Blewett et al. | 6,383,195 B1 | 5/2002 | Richard | |
| 5,997,555 A | 12/1999 | Kontos | 6,383,197 B1 | 5/2002 | Conlon et al. | |
| 6,001,120 A | 12/1999 | Levin | 6,391,029 B1 | 5/2002 | Hooven et al. | |
| 6,004,269 A | 12/1999 | Crowley et al. | 6,402,735 B1 | 6/2002 | Langevin | |
| 6,004,330 A | 12/1999 | Middleman et al. | 6,406,440 B1 | 6/2002 | Stefanchik | |
| 6,007,566 A | 12/1999 | Wenstrom, Jr. | 6,409,727 B1 | 6/2002 | Bales et al. | |
| 6,010,515 A | 1/2000 | Swain et al. | 6,409,733 B1 | 6/2002 | Conlon et al. | |
| 6,012,494 A | 1/2000 | Balazs | 6,427,089 B1 | 7/2002 | Knowlton | |
| 6,017,356 A | 1/2000 | Frederick et al. | 6,431,500 B1 | 8/2002 | Jacobs et al. | |
| 6,019,770 A | 2/2000 | Christoudias | 6,443,970 B1 | 9/2002 | Schulze et al. | |
| 6,024,708 A | 2/2000 | Bales et al. | 6,443,988 B2 | 9/2002 | Felt et al. | |
| 6,024,747 A | 2/2000 | Kontos | 6,447,511 B1 | 9/2002 | Slater | |
| 6,027,522 A | 2/2000 | Palmer | 6,447,523 B1 | 9/2002 | Middleman et al. | |
| 6,030,365 A | 2/2000 | Laufer | 6,454,783 B1 | 9/2002 | Piskun | |
| 6,030,634 A | 2/2000 | Wu et al. | 6,454,785 B2 | 9/2002 | De Hoyos Garza | |
| 6,033,399 A | 3/2000 | Gines | 6,458,076 B1 | 10/2002 | Pruitt | |
| 6,036,685 A | 3/2000 | Mueller | 6,464,701 B1 | 10/2002 | Hooven et al. | |
| 6,053,927 A | 4/2000 | Hamas | 6,464,702 B2 | 10/2002 | Schulze et al. | |
| 6,066,160 A | 5/2000 | Colvin et al. | 6,475,104 B1 | 11/2002 | Lutz et al. | |
| 6,068,603 A | 5/2000 | Suzuki | 6,485,411 B1 | 11/2002 | Konstorum et al. | |
| 6,068,629 A | 5/2000 | Haissaguerre et al. | 6,489,745 B1 | 12/2002 | Koreis | |
| 6,071,233 A | 6/2000 | Ishikawa et al. | 6,491,626 B1 | 12/2002 | Stone et al. | |
| 6,074,408 A | 6/2000 | Freeman | 6,491,627 B1 | 12/2002 | Komi | |
| 6,086,530 A | 7/2000 | Mack | 6,491,691 B1 | 12/2002 | Morley et al. | |
| 6,090,108 A | 7/2000 | McBrayer et al. | 6,493,590 B1 | 12/2002 | Wessman et al. | |
| 6,096,046 A | 8/2000 | Weiss | 6,494,893 B2 | 12/2002 | Dubrul et al. | |
| 6,102,926 A | 8/2000 | Tartaglia et al. | 6,500,176 B1 | 12/2002 | Truckai et al. | |
| 6,106,473 A | 8/2000 | Violante et al. | 6,503,192 B1 | 1/2003 | Ouchi | |
| 6,109,852 A | 8/2000 | Shahinpoor et al. | 6,506,190 B1 | 1/2003 | Walshe | |
| 6,110,154 A | 8/2000 | Shimomura et al. | 6,508,827 B1 | 1/2003 | Manhes | |
| 6,110,183 A | 8/2000 | Cope | 6,514,239 B2 | 2/2003 | Shimmura et al. | |
| 6,113,593 A | 9/2000 | Tu et al. | 6,520,954 B2 | 2/2003 | Ouchi | |
| 6,117,144 A | 9/2000 | Nobles et al. | 6,543,456 B1 | 4/2003 | Freeman | |
| 6,117,158 A | 9/2000 | Measamer et al. | 6,551,270 B1 | 4/2003 | Bimbo et al. | |
| 6,139,555 A | 10/2000 | Hart et al. | 6,554,829 B2 | 4/2003 | Schulze et al. | |
| 6,146,391 A | 11/2000 | Cigaina | 6,558,384 B2 | 5/2003 | Mayenberger | |
| 6,148,222 A | 11/2000 | Ramsey, III | 6,562,035 B1 | 5/2003 | Levin | |
| 6,149,653 A | 11/2000 | Deslauriers | 6,562,052 B2 | 5/2003 | Nobles et al. | |
| 6,149,662 A | 11/2000 | Pugliesi et al. | 6,569,159 B1 | 5/2003 | Edwards et al. | |
| 6,159,200 A | 12/2000 | Verdura et al. | 6,572,629 B2 | 6/2003 | Kalloo et al. | |
| 6,165,184 A | 12/2000 | Verdura et al. | 6,572,635 B2 | 6/2003 | Bonutti | |
| 6,168,570 B1 | 1/2001 | Ferrera | 6,575,988 B2 | 6/2003 | Rousseau | |
| 6,168,605 B1 | 1/2001 | Measamer et al. | 6,579,311 B1 | 6/2003 | Makower | |
| 6,170,130 B1 | 1/2001 | Hamilton et al. | 6,585,642 B2 | 7/2003 | Christopher | |
| 6,179,776 B1 | 1/2001 | Adams et al. | 6,585,717 B1 | 7/2003 | Wittenberger et al. | |
| 6,179,837 B1 | 1/2001 | Hooven | 6,587,750 B2 | 7/2003 | Gerbi et al. | |
| 6,183,420 B1 | 2/2001 | Douk et al. | 6,592,559 B1 | 7/2003 | Pakter et al. | |
| 6,190,353 B1 | 2/2001 | Makower et al. | 6,592,603 B2 | 7/2003 | Lasner | |
| 6,190,384 B1 | 2/2001 | Ouchi | 6,602,262 B2 | 8/2003 | Griego et al. | |
| 6,190,399 B1 | 2/2001 | Palmer et al. | 6,605,105 B1 | 8/2003 | Cuschieri et al. | |
| 6,203,533 B1 | 3/2001 | Ouchi | 6,610,072 B1 | 8/2003 | Christy et al. | |
| 6,206,872 B1 | 3/2001 | Lafond et al. | 6,610,074 B2 | 8/2003 | Santilli | |
| 6,206,877 B1 | 3/2001 | Kese et al. | 6,620,193 B1 | 9/2003 | Lau et al. | |
| 6,214,007 B1 | 4/2001 | Anderson | 6,623,448 B2 | 9/2003 | Slater | |
| 6,228,096 B1 | 5/2001 | Marchand | 6,626,919 B1 | 9/2003 | Swanstrom | |
| 6,234,958 B1 | 5/2001 | Snoke et al. | 6,632,229 B1 * | 10/2003 | Yamanouchi | 606/153 |
| 6,245,079 B1 | 6/2001 | Nobles et al. | 6,638,286 B1 | 10/2003 | Burbank et al. | |
| 6,246,914 B1 | 6/2001 | de la Rama et al. | 6,652,521 B2 | 11/2003 | Schulze | |

| | | |
|---|---|---|
| 6,652,551 B1 | 11/2003 | Heiss |
| 6,656,194 B1 | 12/2003 | Gannoe et al. |
| 6,663,641 B1 | 12/2003 | Kovac et al. |
| 6,666,854 B1 | 12/2003 | Lange |
| 6,672,338 B1 | 1/2004 | Esashi et al. |
| 6,673,058 B2 | 1/2004 | Snow |
| 6,673,087 B1 | 1/2004 | Chang et al. |
| 6,679,882 B1 | 1/2004 | Kornerup |
| 6,685,628 B2 | 2/2004 | Vu |
| 6,685,724 B1 | 2/2004 | Haluck |
| 6,692,445 B2 | 2/2004 | Roberts et al. |
| 6,692,462 B2 | 2/2004 | Mackenzie et al. |
| 6,699,180 B2 | 3/2004 | Kobayashi |
| 6,699,256 B1 | 3/2004 | Logan et al. |
| 6,699,263 B2 | 3/2004 | Cope |
| 6,706,018 B2 | 3/2004 | Westlund et al. |
| 6,708,066 B2 | 3/2004 | Herbst et al. |
| 6,709,445 B2 | 3/2004 | Boebel et al. |
| 6,716,226 B2 | 4/2004 | Sixto, Jr. et al. |
| 6,736,822 B2 | 5/2004 | McClellan et al. |
| 6,740,030 B2 | 5/2004 | Martone et al. |
| 6,743,240 B2 | 6/2004 | Smith et al. |
| 6,749,560 B1 | 6/2004 | Konstorum et al. |
| 6,749,609 B1 | 6/2004 | Lunsford et al. |
| 6,752,768 B2 | 6/2004 | Burdorff et al. |
| 6,752,811 B2 | 6/2004 | Chu et al. |
| 6,752,822 B2 | 6/2004 | Jespersen |
| 6,761,685 B2 | 7/2004 | Adams et al. |
| 6,761,718 B2 | 7/2004 | Madsen |
| 6,773,434 B2 | 8/2004 | Ciarrocca |
| 6,780,151 B2 | 8/2004 | Grabover et al. |
| 6,780,352 B2 | 8/2004 | Jacobson |
| 6,783,491 B2 | 8/2004 | Saadat et al. |
| 6,786,864 B2 | 9/2004 | Matsuura et al. |
| 6,790,173 B2 | 9/2004 | Saadat et al. |
| 6,795,728 B2 | 9/2004 | Chornenky et al. |
| 6,800,056 B2 | 10/2004 | Tartaglia et al. |
| 6,808,491 B2 | 10/2004 | Kortenbach et al. |
| 6,824,548 B2 | 11/2004 | Smith et al. |
| 6,836,688 B2 | 12/2004 | Ingle et al. |
| 6,837,847 B2 | 1/2005 | Ewers et al. |
| 6,843,794 B2 | 1/2005 | Sixto, Jr. et al. |
| 6,861,250 B1 | 3/2005 | Cole et al. |
| 6,866,627 B2 | 3/2005 | Nozue |
| 6,878,106 B1 | 4/2005 | Herrmann |
| 6,878,110 B2 | 4/2005 | Yang et al. |
| 6,881,216 B2 | 4/2005 | Di Caprio et al. |
| 6,884,213 B2 | 4/2005 | Raz et al. |
| 6,887,255 B2 | 5/2005 | Shimm |
| 6,889,089 B2 | 5/2005 | Behl et al. |
| 6,896,683 B1 | 5/2005 | Gadberry et al. |
| 6,896,692 B2 | 5/2005 | Ginn et al. |
| 6,908,427 B2 | 6/2005 | Fleener et al. |
| 6,908,476 B2 | 6/2005 | Jud et al. |
| 6,916,284 B2 | 7/2005 | Moriyama |
| 6,918,871 B2 | 7/2005 | Schulze |
| 6,926,725 B2 | 8/2005 | Cooke et al. |
| 6,932,810 B2 | 8/2005 | Ryan |
| 6,932,824 B1 | 8/2005 | Roop et al. |
| 6,932,827 B2 | 8/2005 | Cole |
| 6,939,327 B2 | 9/2005 | Hall et al. |
| 6,942,613 B2 | 9/2005 | Ewers et al. |
| 6,945,472 B2 | 9/2005 | Wuttke et al. |
| 6,945,979 B2 | 9/2005 | Kortenbach et al. |
| 6,958,035 B2 | 10/2005 | Friedman et al. |
| 6,960,162 B2 | 11/2005 | Saadat et al. |
| 6,960,163 B2 | 11/2005 | Ewers et al. |
| 6,962,587 B2 | 11/2005 | Johnson et al. |
| 6,964,662 B2 | 11/2005 | Kidooka |
| 6,966,909 B2 | 11/2005 | Marshall et al. |
| 6,966,919 B2 | 11/2005 | Sixto, Jr. et al. |
| 6,967,462 B1 | 11/2005 | Landis |
| 6,971,988 B2 | 12/2005 | Orban, III |
| 6,972,017 B2 | 12/2005 | Smith et al. |
| 6,974,411 B2 | 12/2005 | Belson |
| 6,976,992 B2 | 12/2005 | Sachatello et al. |
| 6,984,203 B2 | 1/2006 | Tartaglia et al. |
| 6,984,205 B2 | 1/2006 | Gazdzinski |
| 6,986,774 B2 | 1/2006 | Middleman et al. |
| 6,988,987 B2 | 1/2006 | Ishikawa et al. |
| 6,989,028 B2 | 1/2006 | Lashinski et al. |
| 6,991,627 B2 | 1/2006 | Madhani et al. |
| 6,991,631 B2 | 1/2006 | Woloszko et al. |
| 6,994,708 B2 | 2/2006 | Manzo |
| 6,997,931 B2 | 2/2006 | Sauer et al. |
| 7,000,818 B2 | 2/2006 | Shelton, IV et al. |
| 7,001,341 B2 | 2/2006 | Gellman et al. |
| 7,008,375 B2 | 3/2006 | Weisel |
| 7,009,634 B2 | 3/2006 | Iddan et al. |
| 7,010,340 B2 | 3/2006 | Scarantino et al. |
| 7,020,531 B1 | 3/2006 | Colliou et al. |
| 7,025,580 B2 | 4/2006 | Heagy et al. |
| 7,029,435 B2 | 4/2006 | Nakao |
| 7,029,438 B2 | 4/2006 | Morin et al. |
| 7,029,450 B2 | 4/2006 | Gellman |
| 7,035,680 B2 | 4/2006 | Partridge et al. |
| 7,037,290 B2 | 5/2006 | Gardeski et al. |
| 7,041,052 B2 | 5/2006 | Saadat et al. |
| 7,052,489 B2 | 5/2006 | Griego et al. |
| 7,060,024 B2 | 6/2006 | Long et al. |
| 7,060,025 B2 | 6/2006 | Long et al. |
| 7,063,697 B2 | 6/2006 | Slater |
| 7,063,715 B2 | 6/2006 | Onuki et al. |
| 7,066,879 B2 | 6/2006 | Fowler et al. |
| 7,066,936 B2 | 6/2006 | Ryan |
| 7,070,602 B2 | 7/2006 | Smith et al. |
| 7,076,305 B2 | 7/2006 | Imran et al. |
| 7,083,618 B2 | 8/2006 | Couture et al. |
| 7,083,620 B2 | 8/2006 | Jahns et al. |
| 7,083,629 B2 | 8/2006 | Weller et al. |
| 7,083,635 B2 | 8/2006 | Ginn |
| 7,087,071 B2 | 8/2006 | Nicholas et al. |
| 7,090,673 B2 | 8/2006 | Dycus et al. |
| 7,090,685 B2 | 8/2006 | Kortenbach et al. |
| 7,093,518 B2 | 8/2006 | Gmeilbauer |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,105,000 B2 | 9/2006 | McBrayer |
| 7,105,005 B2 | 9/2006 | Blake |
| 7,108,703 B2 | 9/2006 | Danitz et al. |
| 7,112,208 B2 | 9/2006 | Morris et al. |
| 7,115,092 B2 | 10/2006 | Park et al. |
| 7,117,703 B2 | 10/2006 | Kato et al. |
| 7,118,531 B2 | 10/2006 | Krill |
| 7,118,578 B2 | 10/2006 | West, Jr. et al. |
| 7,118,587 B2 | 10/2006 | Dycus et al. |
| 7,128,708 B2 | 10/2006 | Saadat et al. |
| RE39,415 E | 11/2006 | Bales et al. |
| 7,131,978 B2 | 11/2006 | Sancoff et al. |
| 7,131,979 B2 | 11/2006 | DiCarlo et al. |
| 7,131,980 B1 | 11/2006 | Field et al. |
| 7,137,980 B2 | 11/2006 | Buysse et al. |
| 7,137,981 B2 | 11/2006 | Long |
| 7,146,984 B2 | 12/2006 | Stack et al. |
| 7,147,650 B2 | 12/2006 | Lee |
| 7,150,097 B2 | 12/2006 | Sremcich et al. |
| 7,150,655 B2 | 12/2006 | Mastrototaro et al. |
| 7,152,488 B2 | 12/2006 | Hedrich et al. |
| 7,153,321 B2 | 12/2006 | Andrews |
| 7,163,525 B2 | 1/2007 | Franer |
| 7,172,714 B2 | 2/2007 | Jacobson |
| 7,179,254 B2 | 2/2007 | Pendekanti et al. |
| 7,188,627 B2 | 3/2007 | Nelson et al. |
| 7,195,612 B2 | 3/2007 | Van Sloten et al. |
| 7,195,631 B2 | 3/2007 | Dumbauld |
| 7,204,820 B2 | 4/2007 | Akahoshi |
| 7,208,005 B2 | 4/2007 | Frecker et al. |
| 7,211,092 B2 | 5/2007 | Hughett |
| 7,220,227 B2 | 5/2007 | Sasaki et al. |
| 7,223,272 B2 | 5/2007 | Francese et al. |
| 7,232,414 B2 | 6/2007 | Gonzalez |
| 7,232,445 B2 | 6/2007 | Kortenbach et al. |
| 7,241,290 B2 | 7/2007 | Doyle et al. |
| 7,244,228 B2 | 7/2007 | Lubowski |
| 7,250,027 B2 | 7/2007 | Barry |
| 7,252,660 B2 | 8/2007 | Kunz |
| 7,255,675 B2 | 8/2007 | Gertner et al. |

| Patent | Date | Name |
|---|---|---|
| 7,270,663 B2 | 9/2007 | Nakao |
| 7,294,139 B1 | 11/2007 | Gengler |
| 7,301,250 B2 | 11/2007 | Cassel |
| 7,306,597 B2 | 12/2007 | Manzo |
| 7,308,828 B2 | 12/2007 | Hashimoto |
| 7,318,802 B2 | 1/2008 | Suzuki et al. |
| 7,320,695 B2 | 1/2008 | Carroll |
| 7,322,934 B2 | 1/2008 | Miyake et al. |
| 7,323,006 B2 | 1/2008 | Andreas et al. |
| 7,329,256 B2 | 2/2008 | Johnson et al. |
| 7,329,257 B2 | 2/2008 | Kanehira et al. |
| 7,329,383 B2 | 2/2008 | Stinson |
| 7,344,536 B1 | 3/2008 | Lunsford et al. |
| 7,352,387 B2 | 4/2008 | Yamamoto |
| 7,364,582 B2 | 4/2008 | Lee |
| 7,371,215 B2 | 5/2008 | Colliou et al. |
| 7,381,216 B2 | 6/2008 | Buzzard et al. |
| 7,393,322 B2 | 7/2008 | Wenchell |
| 7,402,162 B2 | 7/2008 | Ouchi |
| 7,404,791 B2 | 7/2008 | Linares et al. |
| 7,413,563 B2 | 8/2008 | Corcoran et al. |
| 7,416,554 B2 | 8/2008 | Lam et al. |
| 7,422,590 B2 | 9/2008 | Kupferschmid et al. |
| 7,435,257 B2 | 10/2008 | Lashinski et al. |
| 7,452,327 B2 | 11/2008 | Durgin et al. |
| 7,455,208 B2 | 11/2008 | Wales et al. |
| 7,468,066 B2 | 12/2008 | Vargas et al. |
| 7,488,295 B2 | 2/2009 | Burbank et al. |
| 7,497,867 B2 | 3/2009 | Lasner et al. |
| 7,507,200 B2 | 3/2009 | Okada |
| 7,524,281 B2 | 4/2009 | Chu et al. |
| 7,524,302 B2 | 4/2009 | Tower |
| 7,534,228 B2 | 5/2009 | Williams |
| 7,540,872 B2 | 6/2009 | Schechter et al. |
| 7,544,203 B2 | 6/2009 | Chin et al. |
| 7,548,040 B2 | 6/2009 | Lee et al. |
| 7,549,564 B2 | 6/2009 | Boudreaux |
| 7,553,278 B2 | 6/2009 | Kucklick |
| 7,553,298 B2 | 6/2009 | Hunt et al. |
| 7,559,887 B2 | 7/2009 | Dannan |
| 7,559,916 B2 | 7/2009 | Smith et al. |
| 7,560,006 B2 | 7/2009 | Rakos et al. |
| 7,561,916 B2 | 7/2009 | Hunt et al. |
| 7,566,334 B2 | 7/2009 | Christian et al. |
| 7,575,144 B2 | 8/2009 | Ortiz et al. |
| 7,575,548 B2 | 8/2009 | Takemoto et al. |
| 7,579,550 B2 | 8/2009 | Dayton et al. |
| 7,582,096 B2 | 9/2009 | Gellman et al. |
| 7,588,177 B2 | 9/2009 | Racenet |
| 7,588,557 B2 | 9/2009 | Nakao |
| 7,618,398 B2 | 11/2009 | Holman et al. |
| 7,632,250 B2 | 12/2009 | Smith et al. |
| 7,635,373 B2 | 12/2009 | Ortiz |
| 7,637,903 B2 | 12/2009 | Lentz et al. |
| 7,651,483 B2 | 1/2010 | Byrum et al. |
| 7,651,509 B2 | 1/2010 | Bojarski et al. |
| 7,654,431 B2 | 2/2010 | Hueil et al. |
| 7,655,004 B2 | 2/2010 | Long |
| 7,662,089 B2 | 2/2010 | Okada et al. |
| 7,666,180 B2 | 2/2010 | Holsten et al. |
| 7,674,259 B2 | 3/2010 | Shadduck |
| 7,713,189 B2 | 5/2010 | Hanke |
| 7,713,270 B2 | 5/2010 | Suzuki |
| 7,736,374 B2 | 6/2010 | Vaughan et al. |
| 7,744,615 B2 | 6/2010 | Couture |
| 7,758,577 B2 | 7/2010 | Nobis et al. |
| 7,762,998 B2 | 7/2010 | Birk et al. |
| 7,771,416 B2 | 8/2010 | Spivey et al. |
| 7,780,683 B2 | 8/2010 | Roue et al. |
| 7,780,691 B2 | 8/2010 | Stefanchik |
| 7,794,409 B2 | 9/2010 | Damarati |
| 7,794,475 B2 | 9/2010 | Hess et al. |
| 7,815,662 B2 | 10/2010 | Spivey et al. |
| 7,828,186 B2 | 11/2010 | Wales |
| 7,837,615 B2 | 11/2010 | Le et al. |
| 7,846,171 B2 | 12/2010 | Kullas et al. |
| 7,850,660 B2 | 12/2010 | Uth et al. |
| 7,857,183 B2 | 12/2010 | Shelton, IV |
| 7,862,546 B2 | 1/2011 | Conlon et al. |
| 7,867,216 B2 | 1/2011 | Wahr et al. |
| 7,892,220 B2 | 2/2011 | Faller et al. |
| 7,896,887 B2 | 3/2011 | Rimbaugh et al. |
| 7,909,809 B2 | 3/2011 | Scopton et al. |
| 7,914,513 B2 | 3/2011 | Voorhees, Jr. |
| 7,918,869 B2 | 4/2011 | Saadat et al. |
| 7,931,624 B2 | 4/2011 | Smith et al. |
| 7,945,332 B2 | 5/2011 | Schechter |
| 7,947,000 B2 | 5/2011 | Vargas et al. |
| 7,955,298 B2 | 6/2011 | Carroll et al. |
| 7,963,975 B2 | 6/2011 | Criscuolo |
| 7,988,685 B2 | 8/2011 | Ziaie et al. |
| 8,075,587 B2 | 12/2011 | Ginn |
| 8,118,821 B2 * | 2/2012 | Mouw ............ 606/153 |
| 2001/0049497 A1 | 12/2001 | Kalloo et al. |
| 2002/0022771 A1 | 2/2002 | Diokno et al. |
| 2002/0022857 A1 | 2/2002 | Goldsteen et al. |
| 2002/0023353 A1 | 2/2002 | Ting-Kung |
| 2002/0029055 A1 | 3/2002 | Bonutti |
| 2002/0042562 A1 | 4/2002 | Meron et al. |
| 2002/0049439 A1 | 4/2002 | Mulier et al. |
| 2002/0068945 A1 | 6/2002 | Sixto, Jr. et al. |
| 2002/0078967 A1 | 6/2002 | Sixto, Jr. et al. |
| 2002/0082516 A1 | 6/2002 | Stefanchik |
| 2002/0091391 A1 | 7/2002 | Cole et al. |
| 2002/0095164 A1 | 7/2002 | Andreas et al. |
| 2002/0107530 A1 | 8/2002 | Sauer et al. |
| 2002/0133115 A1 * | 9/2002 | Gordon et al. ............ 604/96.01 |
| 2002/0138086 A1 | 9/2002 | Sixto, Jr. et al. |
| 2002/0147456 A1 | 10/2002 | Diduch et al. |
| 2002/0183591 A1 | 12/2002 | Matsuura et al. |
| 2003/0023255 A1 | 1/2003 | Miles et al. |
| 2003/0036679 A1 | 2/2003 | Kortenbach et al. |
| 2003/0069602 A1 | 4/2003 | Jacobs et al. |
| 2003/0083681 A1 | 5/2003 | Moutafis et al. |
| 2003/0114732 A1 | 6/2003 | Webler et al. |
| 2003/0120257 A1 | 6/2003 | Houston et al. |
| 2003/0124009 A1 | 7/2003 | Ravi et al. |
| 2003/0130564 A1 | 7/2003 | Martone et al. |
| 2003/0130656 A1 | 7/2003 | Levin |
| 2003/0158521 A1 | 8/2003 | Ameri |
| 2003/0167062 A1 | 9/2003 | Gambale et al. |
| 2003/0171651 A1 | 9/2003 | Page et al. |
| 2003/0176880 A1 | 9/2003 | Long et al. |
| 2003/0191497 A1 | 10/2003 | Cope |
| 2003/0195565 A1 | 10/2003 | Bonutti |
| 2003/0216611 A1 | 11/2003 | Vu |
| 2003/0216615 A1 | 11/2003 | Ouchi |
| 2003/0220545 A1 | 11/2003 | Ouchi |
| 2003/0225312 A1 | 12/2003 | Suzuki et al. |
| 2003/0225332 A1 | 12/2003 | Okada et al. |
| 2003/0229269 A1 | 12/2003 | Humphrey |
| 2003/0229371 A1 | 12/2003 | Whitworth |
| 2003/0236549 A1 | 12/2003 | Bonadio et al. |
| 2004/0002683 A1 | 1/2004 | Nicholson et al. |
| 2004/0002735 A1 | 1/2004 | Lizardi et al. |
| 2004/0034369 A1 | 2/2004 | Sauer et al. |
| 2004/0098007 A1 | 5/2004 | Heiss |
| 2004/0101456 A1 | 5/2004 | Kuroshima et al. |
| 2004/0116948 A1 | 6/2004 | Sixto, Jr. et al. |
| 2004/0127940 A1 | 7/2004 | Ginn et al. |
| 2004/0133077 A1 | 7/2004 | Obenchain et al. |
| 2004/0133089 A1 | 7/2004 | Kilcoyne et al. |
| 2004/0136779 A1 | 7/2004 | Bhaskar |
| 2004/0138525 A1 | 7/2004 | Saadat et al. |
| 2004/0138529 A1 | 7/2004 | Wiltshire et al. |
| 2004/0138587 A1 | 7/2004 | Lyons, IV |
| 2004/0161451 A1 | 8/2004 | Pierce et al. |
| 2004/0186350 A1 | 9/2004 | Brenneman et al. |
| 2004/0193009 A1 | 9/2004 | Jaffe et al. |
| 2004/0193146 A1 | 9/2004 | Lee et al. |
| 2004/0193186 A1 | 9/2004 | Kortenbach et al. |
| 2004/0193188 A1 | 9/2004 | Francese |
| 2004/0193189 A1 | 9/2004 | Kortenbach et al. |
| 2004/0193200 A1 | 9/2004 | Dworschak et al. |
| 2004/0199052 A1 | 10/2004 | Banik et al. |
| 2004/0206859 A1 | 10/2004 | Chong et al. |
| 2004/0210245 A1 | 10/2004 | Erickson et al. |
| 2004/0215058 A1 | 10/2004 | Zirps et al. |

| | | | | | |
|---|---|---|---|---|---|
| 2004/0225183 A1 | 11/2004 | Michlitsch et al. | 2005/0288555 A1 | 12/2005 | Binmoeller |
| 2004/0225186 A1 | 11/2004 | Horne, Jr. et al. | 2006/0004406 A1 | 1/2006 | Wehrstein et al. |
| 2004/0230095 A1 | 11/2004 | Stefanchik et al. | 2006/0004409 A1 | 1/2006 | Nobis et al. |
| 2004/0230096 A1 | 11/2004 | Stefanchik et al. | 2006/0004410 A1 | 1/2006 | Nobis et al. |
| 2004/0230097 A1 | 11/2004 | Stefanchik et al. | 2006/0015009 A1 | 1/2006 | Jaffe et al. |
| 2004/0230161 A1 | 11/2004 | Zeiner | 2006/0020167 A1 | 1/2006 | Sitzmann |
| 2004/0249246 A1 | 12/2004 | Campos | 2006/0020247 A1 | 1/2006 | Kagan et al. |
| 2004/0249367 A1 | 12/2004 | Saadat et al. | 2006/0025654 A1 | 2/2006 | Suzuki et al. |
| 2004/0249394 A1 | 12/2004 | Morris et al. | 2006/0025781 A1 | 2/2006 | Young et al. |
| 2004/0249443 A1 | 12/2004 | Shanley et al. | 2006/0025812 A1 | 2/2006 | Shelton, IV |
| 2005/0004515 A1 | 1/2005 | Hart et al. | 2006/0025819 A1 | 2/2006 | Nobis et al. |
| 2005/0033265 A1 | 2/2005 | Engel et al. | 2006/0036267 A1 | 2/2006 | Saadat et al. |
| 2005/0033277 A1 | 2/2005 | Clague et al. | 2006/0041188 A1 | 2/2006 | Dirusso et al. |
| 2005/0033319 A1 | 2/2005 | Gambale et al. | 2006/0058582 A1 | 3/2006 | Maahs et al. |
| 2005/0033333 A1 | 2/2005 | Smith et al. | 2006/0058776 A1 | 3/2006 | Bilsbury |
| 2005/0043690 A1 | 2/2005 | Todd | 2006/0069396 A1 | 3/2006 | Meade et al. |
| 2005/0049616 A1 | 3/2005 | Rivera et al. | 2006/0069424 A1 | 3/2006 | Acosta et al. |
| 2005/0065397 A1 | 3/2005 | Saadat et al. | 2006/0069425 A1 | 3/2006 | Hillis et al. |
| 2005/0065517 A1 | 3/2005 | Chin | 2006/0074413 A1 | 4/2006 | Behzadian |
| 2005/0070754 A1 | 3/2005 | Nobis et al. | 2006/0079890 A1 | 4/2006 | Guerra |
| 2005/0070763 A1 | 3/2005 | Nobis et al. | 2006/0089528 A1 | 4/2006 | Tartaglia et al. |
| 2005/0070764 A1 | 3/2005 | Nobis et al. | 2006/0095031 A1 | 5/2006 | Ormsby |
| 2005/0080413 A1 | 4/2005 | Canady | 2006/0095060 A1 | 5/2006 | Mayenberger et al. |
| 2005/0085693 A1 | 4/2005 | Belson et al. | 2006/0100687 A1 | 5/2006 | Fahey et al. |
| 2005/0085832 A1 | 4/2005 | Sancoff et al. | 2006/0106423 A1 | 5/2006 | Weisel et al. |
| 2005/0090837 A1 | 4/2005 | Sixto, Jr. et al. | 2006/0111209 A1 | 5/2006 | Hinman et al. |
| 2005/0090838 A1 | 4/2005 | Sixto, Jr. et al. | 2006/0111210 A1 | 5/2006 | Hinman |
| 2005/0101837 A1 | 5/2005 | Kalloo et al. | 2006/0111704 A1 | 5/2006 | Brenneman et al. |
| 2005/0101838 A1 | 5/2005 | Camillocci et al. | 2006/0129166 A1 | 6/2006 | Lavelle |
| 2005/0107663 A1 | 5/2005 | Saadat et al. | 2006/0135962 A1 | 6/2006 | Kick et al. |
| 2005/0107664 A1 | 5/2005 | Kalloo et al. | 2006/0135971 A1 | 6/2006 | Swanstrom et al. |
| 2005/0110881 A1 | 5/2005 | Glukhovsky et al. | 2006/0135984 A1 | 6/2006 | Kramer et al. |
| 2005/0113847 A1 | 5/2005 | Gadberry et al. | 2006/0142644 A1 | 6/2006 | Mulac et al. |
| 2005/0119613 A1 | 6/2005 | Moenning et al. | 2006/0142652 A1 | 6/2006 | Keenan |
| 2005/0124855 A1 | 6/2005 | Jaffe et al. | 2006/0142790 A1 | 6/2006 | Gertner |
| 2005/0125010 A1 | 6/2005 | Smith et al. | 2006/0142798 A1 | 6/2006 | Holman et al. |
| 2005/0131279 A1 | 6/2005 | Boulais et al. | 2006/0149131 A1 | 7/2006 | Or |
| 2005/0131457 A1 | 6/2005 | Douglas et al. | 2006/0149132 A1 | 7/2006 | Iddan |
| 2005/0137454 A1 | 6/2005 | Saadat et al. | 2006/0149135 A1 | 7/2006 | Paz |
| 2005/0143647 A1 | 6/2005 | Minai et al. | 2006/0161190 A1 | 7/2006 | Gadberry et al. |
| 2005/0143690 A1 | 6/2005 | High | 2006/0167416 A1 | 7/2006 | Mathis et al. |
| 2005/0143774 A1 | 6/2005 | Polo | 2006/0167482 A1 | 7/2006 | Swain et al. |
| 2005/0143803 A1 | 6/2005 | Watson et al. | 2006/0178560 A1 | 8/2006 | Saadat et al. |
| 2005/0149087 A1 | 7/2005 | Ahlberg et al. | 2006/0183975 A1 | 8/2006 | Saadat et al. |
| 2005/0149096 A1 | 7/2005 | Hilal et al. | 2006/0184161 A1 | 8/2006 | Maahs et al. |
| 2005/0159648 A1 | 7/2005 | Freed | 2006/0189844 A1 | 8/2006 | Tien |
| 2005/0165272 A1 | 7/2005 | Okada et al. | 2006/0189845 A1 | 8/2006 | Maahs et al. |
| 2005/0165378 A1 | 7/2005 | Heinrich et al. | 2006/0190027 A1 | 8/2006 | Downey |
| 2005/0165411 A1 | 7/2005 | Orban, III | 2006/0195084 A1 | 8/2006 | Slater |
| 2005/0165429 A1 | 7/2005 | Douglas et al. | 2006/0200005 A1 | 9/2006 | Bjork et al. |
| 2005/0182429 A1* | 8/2005 | Yamanouchi ................ 606/153 | 2006/0200169 A1 | 9/2006 | Sniffin |
| 2005/0192478 A1 | 9/2005 | Williams et al. | 2006/0200170 A1 | 9/2006 | Aranyi |
| 2005/0192598 A1 | 9/2005 | Johnson et al. | 2006/0200199 A1 | 9/2006 | Bonutti et al. |
| 2005/0192602 A1 | 9/2005 | Manzo | 2006/0217665 A1 | 9/2006 | Prosek |
| 2005/0192654 A1 | 9/2005 | Chanduszko et al. | 2006/0217697 A1 | 9/2006 | Lau et al. |
| 2005/0209624 A1 | 9/2005 | Vijay | 2006/0217742 A1 | 9/2006 | Messerly et al. |
| 2005/0215858 A1 | 9/2005 | Vail | 2006/0217743 A1 | 9/2006 | Messerly et al. |
| 2005/0216050 A1 | 9/2005 | Sepetka et al. | 2006/0229639 A1 | 10/2006 | Whitfield |
| 2005/0228406 A1 | 10/2005 | Bose | 2006/0229640 A1 | 10/2006 | Whitfield |
| 2005/0234297 A1 | 10/2005 | Devierre et al. | 2006/0237022 A1 | 10/2006 | Chen et al. |
| 2005/0250983 A1 | 11/2005 | Tremaglio et al. | 2006/0237023 A1 | 10/2006 | Cox et al. |
| 2005/0250990 A1 | 11/2005 | Le et al. | 2006/0241570 A1 | 10/2006 | Wilk |
| 2005/0250993 A1 | 11/2005 | Jaeger | 2006/0247576 A1 | 11/2006 | Poncet |
| 2005/0251166 A1 | 11/2005 | Vaughan et al. | 2006/0247673 A1 | 11/2006 | Voegele et al. |
| 2005/0251176 A1 | 11/2005 | Swanstrom et al. | 2006/0253004 A1 | 11/2006 | Frisch et al. |
| 2005/0261674 A1 | 11/2005 | Nobis et al. | 2006/0253039 A1 | 11/2006 | McKenna et al. |
| 2005/0267492 A1 | 12/2005 | Poncet et al. | 2006/0258907 A1 | 11/2006 | Stefanchik et al. |
| 2005/0272975 A1 | 12/2005 | McWeeney et al. | 2006/0258908 A1 | 11/2006 | Stefanchik et al. |
| 2005/0272977 A1 | 12/2005 | Saadat et al. | 2006/0258910 A1 | 11/2006 | Stefanchik et al. |
| 2005/0273084 A1 | 12/2005 | Hinman et al. | 2006/0258954 A1 | 11/2006 | Timberlake et al. |
| 2005/0277945 A1 | 12/2005 | Saadat et al. | 2006/0258955 A1 | 11/2006 | Hoffman et al. |
| 2005/0277951 A1 | 12/2005 | Smith et al. | 2006/0259010 A1 | 11/2006 | Stefanchik et al. |
| 2005/0277952 A1 | 12/2005 | Arp et al. | 2006/0264752 A1 | 11/2006 | Rubinsky et al. |
| 2005/0277954 A1 | 12/2005 | Smith et al. | 2006/0264904 A1 | 11/2006 | Kerby et al. |
| 2005/0277955 A1 | 12/2005 | Palmer et al. | 2006/0264930 A1 | 11/2006 | Nishimura |
| 2005/0277956 A1 | 12/2005 | Francese et al. | 2006/0270902 A1 | 11/2006 | Igarashi et al. |
| 2005/0277957 A1 | 12/2005 | Kuhns et al. | 2006/0271102 A1 | 11/2006 | Bosshard et al. |
| 2005/0283118 A1 | 12/2005 | Uth et al. | 2006/0276835 A1 | 12/2006 | Uchida |
| 2005/0283119 A1 | 12/2005 | Uth et al. | 2006/0281970 A1 | 12/2006 | Stokes et al. |

| | | | | | | |
|---|---|---|---|---|---|---|
| 2006/0282106 A1 | 12/2006 | Cole et al. | | 2007/0293727 A1 | 12/2007 | Goldfarb et al. |
| 2006/0285732 A1 | 12/2006 | Horn et al. | | 2007/0299387 A1 | 12/2007 | Williams et al. |
| 2006/0287644 A1 | 12/2006 | Inganas et al. | | 2008/0004650 A1 | 1/2008 | George |
| 2006/0287666 A1 | 12/2006 | Saadat et al. | | 2008/0015409 A1 | 1/2008 | Barlow et al. |
| 2006/0293626 A1 | 12/2006 | Byrum et al. | | 2008/0015552 A1 | 1/2008 | Doyle et al. |
| 2007/0002135 A1 | 1/2007 | Glukhovsky | | 2008/0021416 A1 | 1/2008 | Arai et al. |
| 2007/0005019 A1 | 1/2007 | Okishige | | 2008/0022927 A1 | 1/2008 | Zhang et al. |
| 2007/0010801 A1 | 1/2007 | Chen et al. | | 2008/0027387 A1 | 1/2008 | Grabinsky |
| 2007/0015965 A1 | 1/2007 | Cox et al. | | 2008/0033451 A1 | 2/2008 | Rieber et al. |
| 2007/0016225 A1 | 1/2007 | Nakao | | 2008/0051629 A1 | 2/2008 | Sugiyama et al. |
| 2007/0032700 A1 | 2/2007 | Fowler et al. | | 2008/0051735 A1 | 2/2008 | Measamer et al. |
| 2007/0032701 A1 | 2/2007 | Fowler et al. | | 2008/0058586 A1 | 3/2008 | Karpiel |
| 2007/0043261 A1 | 2/2007 | Watanabe et al. | | 2008/0065169 A1 | 3/2008 | Colliou et al. |
| 2007/0043345 A1 | 2/2007 | Davalos et al. | | 2008/0071264 A1 | 3/2008 | Azure |
| 2007/0049800 A1 | 3/2007 | Boulais | | 2008/0086172 A1 | 4/2008 | Martin et al. |
| 2007/0049902 A1 | 3/2007 | Griffin et al. | | 2008/0097159 A1 | 4/2008 | Ishiguro |
| 2007/0051375 A1 | 3/2007 | Milliman | | 2008/0097472 A1 | 4/2008 | Agmon et al. |
| 2007/0060880 A1 | 3/2007 | Gregorich et al. | | 2008/0097483 A1 | 4/2008 | Ortiz et al. |
| 2007/0067017 A1 | 3/2007 | Trapp | | 2008/0103527 A1 | 5/2008 | Martin et al. |
| 2007/0073102 A1 | 3/2007 | Matsuno et al. | | 2008/0114384 A1 * | 5/2008 | Chang et al. .................. 606/153 |
| 2007/0073269 A1 | 3/2007 | Becker | | 2008/0119870 A1 | 5/2008 | Williams |
| 2007/0079924 A1 | 4/2007 | Saadat et al. | | 2008/0119891 A1 | 5/2008 | Miles et al. |
| 2007/0088370 A1 | 4/2007 | Kahle et al. | | 2008/0125796 A1 | 5/2008 | Graham |
| 2007/0100375 A1 | 5/2007 | Mikkaichi et al. | | 2008/0132892 A1 | 6/2008 | Lunsford et al. |
| 2007/0100376 A1 | 5/2007 | Mikkaichi et al. | | 2008/0139882 A1 | 6/2008 | Fujimori |
| 2007/0106118 A1 | 5/2007 | Moriyama | | 2008/0147113 A1 | 6/2008 | Nobis et al. |
| 2007/0112251 A1 | 5/2007 | Nakhuda | | 2008/0171907 A1 | 7/2008 | Long et al. |
| 2007/0112331 A1 | 5/2007 | Weber et al. | | 2008/0177135 A1 | 7/2008 | Muyari et al. |
| 2007/0112342 A1 | 5/2007 | Pearson et al. | | 2008/0188868 A1 | 8/2008 | Weitzner et al. |
| 2007/0112383 A1 | 5/2007 | Conlon et al. | | 2008/0200755 A1 | 8/2008 | Bakos |
| 2007/0112384 A1 | 5/2007 | Conlon et al. | | 2008/0200762 A1 | 8/2008 | Stokes et al. |
| 2007/0112385 A1 | 5/2007 | Conlon | | 2008/0200911 A1 | 8/2008 | Long |
| 2007/0112417 A1 | 5/2007 | Shanley et al. | | 2008/0200933 A1 | 8/2008 | Bakos et al. |
| 2007/0112425 A1 | 5/2007 | Schaller et al. | | 2008/0200934 A1 | 8/2008 | Fox |
| 2007/0118115 A1 | 5/2007 | Artale et al. | | 2008/0208213 A1 | 8/2008 | Benjamin et al. |
| 2007/0123840 A1 | 5/2007 | Cox | | 2008/0221587 A1 | 9/2008 | Schwartz |
| 2007/0129605 A1 | 6/2007 | Schaaf | | 2008/0228213 A1 | 9/2008 | Blakeney et al. |
| 2007/0129719 A1 | 6/2007 | Kendale et al. | | 2008/0230972 A1 | 9/2008 | Ganley |
| 2007/0129760 A1 | 6/2007 | Demarais et al. | | 2008/0234696 A1 | 9/2008 | Taylor et al. |
| 2007/0135709 A1 | 6/2007 | Rioux et al. | | 2008/0243106 A1 | 10/2008 | Coe et al. |
| 2007/0135803 A1 | 6/2007 | Belson | | 2008/0243148 A1 | 10/2008 | Mikkaichi et al. |
| 2007/0142706 A1 | 6/2007 | Matsui et al. | | 2008/0243176 A1 | 10/2008 | Weitzner et al. |
| 2007/0142780 A1 | 6/2007 | Van Lue | | 2008/0249567 A1 | 10/2008 | Kaplan |
| 2007/0154460 A1 | 7/2007 | Kraft et al. | | 2008/0262540 A1 | 10/2008 | Bangera et al. |
| 2007/0156028 A1 | 7/2007 | Van Lue et al. | | 2008/0269782 A1 | 10/2008 | Stefanchik et al. |
| 2007/0156127 A1 | 7/2007 | Rioux et al. | | 2008/0269783 A1 | 10/2008 | Griffith |
| 2007/0161855 A1 | 7/2007 | Mikkaichi et al. | | 2008/0275474 A1 | 11/2008 | Martin et al. |
| 2007/0162101 A1 | 7/2007 | Burgermeister et al. | | 2008/0275475 A1 | 11/2008 | Schwemberger et al. |
| 2007/0173691 A1 | 7/2007 | Yokoi et al. | | 2008/0287737 A1 | 11/2008 | Dejima |
| 2007/0173869 A1 | 7/2007 | Gannoe et al. | | 2008/0287983 A1 | 11/2008 | Smith et al. |
| 2007/0173870 A2 | 7/2007 | Zacharias | | 2008/0300461 A1 | 12/2008 | Shaw et al. |
| 2007/0173872 A1 | 7/2007 | Neuenfeldt | | 2008/0300547 A1 | 12/2008 | Bakos |
| 2007/0179525 A1 | 8/2007 | Frecker et al. | | 2008/0309758 A1 | 12/2008 | Karasawa et al. |
| 2007/0179530 A1 | 8/2007 | Tieu et al. | | 2008/0312496 A1 | 12/2008 | Zwolinski |
| 2007/0197865 A1 | 8/2007 | Miyake et al. | | 2008/0312499 A1 | 12/2008 | Handa et al. |
| 2007/0198057 A1 | 8/2007 | Gelbart et al. | | 2008/0312500 A1 | 12/2008 | Asada et al. |
| 2007/0203487 A1 | 8/2007 | Sugita | | 2008/0312506 A1 | 12/2008 | Spivey et al. |
| 2007/0208336 A1 | 9/2007 | Kim et al. | | 2008/0319436 A1 | 12/2008 | Daniel et al. |
| 2007/0208364 A1 | 9/2007 | Smith et al. | | 2008/0319439 A1 | 12/2008 | Ootsubu |
| 2007/0213754 A1 | 9/2007 | Mikkaichi et al. | | 2009/0054728 A1 | 2/2009 | Trusty |
| 2007/0225554 A1 | 9/2007 | Maseda et al. | | 2009/0062788 A1 | 3/2009 | Long et al. |
| 2007/0233040 A1 | 10/2007 | Macnamara et al. | | 2009/0062792 A1 | 3/2009 | Vakharia et al. |
| 2007/0244358 A1 | 10/2007 | Lee | | 2009/0062795 A1 | 3/2009 | Vakharia et al. |
| 2007/0250038 A1 | 10/2007 | Boulais | | 2009/0069634 A1 | 3/2009 | Larkin |
| 2007/0250057 A1 | 10/2007 | Nobis et al. | | 2009/0076499 A1 | 3/2009 | Azure |
| 2007/0255096 A1 | 11/2007 | Stefanchik et al. | | 2009/0078736 A1 | 3/2009 | Van Lue |
| 2007/0255100 A1 | 11/2007 | Barlow et al. | | 2009/0082776 A1 | 3/2009 | Cresina |
| 2007/0255273 A1 | 11/2007 | Fernandez et al. | | 2009/0082779 A1 | 3/2009 | Nakao |
| 2007/0255303 A1 | 11/2007 | Bakos et al. | | 2009/0112059 A1 | 4/2009 | Nobis |
| 2007/0255306 A1 | 11/2007 | Conlon et al. | | 2009/0112062 A1 | 4/2009 | Bakos |
| 2007/0260112 A1 | 11/2007 | Rahmani | | 2009/0112063 A1 | 4/2009 | Bakos et al. |
| 2007/0260117 A1 | 11/2007 | Zwolinski et al. | | 2009/0125042 A1 * | 5/2009 | Mouw .................. 606/153 |
| 2007/0260121 A1 | 11/2007 | Bakos et al. | | 2009/0131751 A1 | 5/2009 | Spivey et al. |
| 2007/0260273 A1 | 11/2007 | Cropper et al. | | 2009/0131932 A1 | 5/2009 | Vakharia et al. |
| 2007/0270629 A1 | 11/2007 | Charles | | 2009/0131933 A1 | 5/2009 | Ghabrial et al. |
| 2007/0270889 A1 | 11/2007 | Conlon et al. | | 2009/0143639 A1 | 6/2009 | Stark |
| 2007/0270895 A1 | 11/2007 | Nobis et al. | | 2009/0143649 A1 | 6/2009 | Rossi |
| 2007/0270907 A1 | 11/2007 | Stokes et al. | | 2009/0143794 A1 | 6/2009 | Conlon et al. |
| 2007/0282371 A1 | 12/2007 | Lee et al. | | 2009/0143818 A1 | 6/2009 | Faller et al. |

| | | |
|---|---|---|
| 2009/0149710 A1 | 6/2009 | Stefanchik et al. |
| 2009/0177031 A1 | 7/2009 | Surti et al. |
| 2009/0177219 A1 | 7/2009 | Conlon |
| 2009/0182332 A1 | 7/2009 | Long et al. |
| 2009/0192344 A1 | 7/2009 | Bakos et al. |
| 2009/0192534 A1 | 7/2009 | Ortiz et al. |
| 2009/0198231 A1 | 8/2009 | Esser et al. |
| 2009/0198253 A1 | 8/2009 | Omori |
| 2009/0216248 A1 | 8/2009 | Uenohara et al. |
| 2009/0248055 A1 | 10/2009 | Spivey et al. |
| 2009/0281559 A1 | 11/2009 | Swain et al. |
| 2009/0287206 A1 | 11/2009 | Jun |
| 2009/0287236 A1 | 11/2009 | Bakos et al. |
| 2009/0292164 A1 | 11/2009 | Yamatani |
| 2009/0299135 A1 | 12/2009 | Spivey |
| 2009/0299143 A1 | 12/2009 | Conlon et al. |
| 2009/0299362 A1 | 12/2009 | Long et al. |
| 2009/0299385 A1 | 12/2009 | Stefanchik et al. |
| 2009/0299406 A1 | 12/2009 | Swain et al. |
| 2009/0299409 A1 | 12/2009 | Coe et al. |
| 2009/0306658 A1 | 12/2009 | Nobis et al. |
| 2009/0306683 A1 | 12/2009 | Zwolinski et al. |
| 2009/0322864 A1 | 12/2009 | Karasawa et al. |
| 2009/0326561 A1 | 12/2009 | Carroll, II et al. |
| 2010/0010294 A1 | 1/2010 | Conlon et al. |
| 2010/0010298 A1 | 1/2010 | Bakos et al. |
| 2010/0010299 A1 | 1/2010 | Bakos et al. |
| 2010/0010303 A1 | 1/2010 | Bakos |
| 2010/0010510 A1 | 1/2010 | Stefanchik |
| 2010/0010511 A1 | 1/2010 | Harris et al. |
| 2010/0023032 A1* | 1/2010 | Granja Filho ............... 606/153 |
| 2010/0036198 A1 | 2/2010 | Tacchino et al. |
| 2010/0042045 A1 | 2/2010 | Spivey |
| 2010/0048990 A1 | 2/2010 | Bakos |
| 2010/0049190 A1 | 2/2010 | Long et al. |
| 2010/0049223 A1* | 2/2010 | Granja Filho ............... 606/153 |
| 2010/0056861 A1 | 3/2010 | Spivey |
| 2010/0056862 A1 | 3/2010 | Bakos |
| 2010/0057085 A1 | 3/2010 | Holcomb et al. |
| 2010/0057108 A1 | 3/2010 | Spivey et al. |
| 2010/0063538 A1 | 3/2010 | Spivey et al. |
| 2010/0076451 A1 | 3/2010 | Zwolinski et al. |
| 2010/0081877 A1 | 4/2010 | Vakharia |
| 2010/0087813 A1 | 4/2010 | Long |
| 2010/0113872 A1 | 5/2010 | Asada et al. |
| 2010/0121362 A1* | 5/2010 | Clague et al. ............... 606/159 |
| 2010/0130817 A1 | 5/2010 | Conlon |
| 2010/0130975 A1 | 5/2010 | Long |
| 2010/0131005 A1 | 5/2010 | Conlon |
| 2010/0152539 A1 | 6/2010 | Ghabrial et al. |
| 2010/0152609 A1 | 6/2010 | Zwolinski et al. |
| 2010/0152746 A1 | 6/2010 | Ceniccola et al. |
| 2010/0179510 A1 | 7/2010 | Fox et al. |
| 2010/0179530 A1 | 7/2010 | Long et al. |
| 2010/0191050 A1 | 7/2010 | Zwolinski |
| 2010/0191267 A1 | 7/2010 | Fox |
| 2010/0198005 A1 | 8/2010 | Fox |
| 2010/0198149 A1 | 8/2010 | Fox |
| 2010/0198244 A1 | 8/2010 | Spivey et al. |
| 2010/0198248 A1 | 8/2010 | Vakharia |
| 2010/0249700 A1 | 9/2010 | Spivey |
| 2010/0286791 A1* | 11/2010 | Goldsmith ................. 623/23.7 |
| 2010/0298642 A1 | 11/2010 | Trusty et al. |
| 2010/0312056 A1 | 12/2010 | Galperin et al. |
| 2010/0331622 A2 | 12/2010 | Conlon |
| 2010/0331774 A2 | 12/2010 | Spivey |
| 2011/0093009 A1 | 4/2011 | Fox |
| 2011/0098694 A1 | 4/2011 | Long |
| 2011/0098704 A1 | 4/2011 | Long et al. |
| 2011/0105850 A1 | 5/2011 | Voegele et al. |
| 2011/0112434 A1 | 5/2011 | Ghabrial et al. |
| 2011/0115891 A1 | 5/2011 | Trusty |
| 2011/0124964 A1 | 5/2011 | Nobis |
| 2011/0152609 A1 | 6/2011 | Trusty et al. |
| 2011/0152610 A1 | 6/2011 | Trusty et al. |
| 2011/0152612 A1 | 6/2011 | Trusty et al. |
| 2011/0152858 A1 | 6/2011 | Long et al. |
| 2011/0152859 A1 | 6/2011 | Long et al. |
| 2011/0152878 A1 | 6/2011 | Trusty et al. |
| 2011/0152923 A1 | 6/2011 | Fox |
| 2011/0160514 A1 | 6/2011 | Long et al. |
| 2011/0190659 A1 | 8/2011 | Long et al. |
| 2011/0190764 A1 | 8/2011 | Long et al. |
| 2011/0245619 A1 | 10/2011 | Holcomb |
| 2011/0306971 A1 | 12/2011 | Long |
| 2012/0004502 A1 | 1/2012 | Weitzner et al. |

FOREIGN PATENT DOCUMENTS

| | | |
|---|---|---|
| DE | 3008120 A1 | 9/1980 |
| DE | 4323585 A1 | 1/1995 |
| DE | 19713797 A1 | 10/1997 |
| DE | 19757056 B4 | 8/2008 |
| DE | 102006027873 B4 | 10/2009 |
| EP | 0086338 A1 | 8/1983 |
| EP | 0286415 A2 | 10/1988 |
| EP | 0589454 A2 | 3/1994 |
| EP | 0464479 B1 | 3/1995 |
| EP | 0529675 B1 | 2/1996 |
| EP | 0724863 B1 | 7/1999 |
| EP | 0760629 B1 | 11/1999 |
| EP | 0818974 B1 | 7/2001 |
| EP | 1281356 A2 | 2/2003 |
| EP | 0947166 B1 | 5/2003 |
| EP | 0836832 B1 | 12/2003 |
| EP | 1402837 A1 | 3/2004 |
| EP | 0744918 B1 | 4/2004 |
| EP | 0931515 B1 | 8/2004 |
| EP | 0941128 B1 | 10/2004 |
| EP | 1411843 B1 | 10/2004 |
| EP | 1150614 B1 | 11/2004 |
| EP | 1477104 A1 | 11/2004 |
| EP | 1481642 A1 | 12/2004 |
| EP | 1493391 A1 | 1/2005 |
| EP | 0848598 B1 | 2/2005 |
| EP | 1281360 B1 | 3/2005 |
| EP | 1568330 A1 | 8/2005 |
| EP | 1452143 B1 | 9/2005 |
| EP | 1616527 A2 | 1/2006 |
| EP | 1006888 B1 | 3/2006 |
| EP | 1629764 A1 | 3/2006 |
| EP | 1013229 B1 | 6/2006 |
| EP | 1721561 A1 | 11/2006 |
| EP | 1153578 B1 | 3/2007 |
| EP | 1334696 B1 | 3/2007 |
| EP | 1769766 A1 | 4/2007 |
| EP | 1836971 A2 | 9/2007 |
| EP | 1836980 A1 | 9/2007 |
| EP | 1854421 A2 | 11/2007 |
| EP | 1857061 A1 | 11/2007 |
| EP | 1875876 A1 | 1/2008 |
| EP | 1891881 A1 | 2/2008 |
| EP | 1902663 A1 | 3/2008 |
| EP | 1477106 B1 | 6/2008 |
| EP | 1949844 A1 | 7/2008 |
| EP | 1518499 B1 | 8/2008 |
| EP | 1709918 B1 | 10/2008 |
| EP | 1985226 A2 | 10/2008 |
| EP | 1994904 A1 | 11/2008 |
| EP | 1707130 B1 | 12/2008 |
| EP | 0723462 B1 | 3/2009 |
| EP | 1769749 B1 | 11/2009 |
| EP | 1493397 B1 | 9/2011 |
| FR | 2731610 A | 9/1996 |
| GB | 330629 A | 6/1930 |
| GB | 2335860 A | 10/1999 |
| GB | 2403909 A | 1/2005 |
| GB | 2421190 A | 6/2006 |
| GB | 2443261 A | 4/2008 |
| JP | 56-46674 | 4/1981 |
| JP | 63309252 A | 12/1988 |
| JP | 4038960 A | 2/1992 |
| JP | 8-29699 A | 2/1996 |
| JP | 2000245683 A | 9/2000 |
| JP | 2002-369791 A | 12/2002 |
| JP | 2003-088494 A | 3/2003 |
| JP | 2003-235852 A | 8/2003 |
| JP | 2004-33525 A | 2/2004 |
| JP | 2004-065745 A | 3/2004 |

| | | | |
|---|---|---|---|
| JP | 2005-121947 A | 5/2005 | |
| JP | 2005-261514 A | 9/2005 | |
| JP | 2006297005 A | 11/2006 | |
| NL | 1021295 C2 | 2/2004 | |
| SU | 194230 | 5/1967 | |
| SU | 980703 | 12/1982 | |
| WO | WO 84/01707 A1 | 5/1984 | |
| WO | WO 92/13494 A1 | 8/1992 | |
| WO | WO 93/10850 A1 | 6/1993 | |
| WO | WO 93/20760 A1 | 10/1993 | |
| WO | WO 93/20765 A1 | 10/1993 | |
| WO | WO 95/09666 A1 | 4/1995 | |
| WO | WO 96/22056 A1 | 7/1996 | |
| WO | WO 96/27331 A1 | 9/1996 | |
| WO | WO 96/39946 A1 | 12/1996 | |
| WO | WO 97/12557 A1 | 4/1997 | |
| WO | WO 98/01080 A1 | 1/1998 | |
| WO | WO 99/00060 A1 | 1/1999 | |
| WO | WO 99/09919 A1 | 3/1999 | |
| WO | WO 99/17661 A1 | 4/1999 | |
| WO | WO 99/30622 A2 | 6/1999 | |
| WO | WO 00/35358 A1 | 6/2000 | |
| WO | WO 01/10319 A1 | 2/2001 | |
| WO | WO 01/26708 A1 | 4/2001 | |
| WO | WO 01/41627 A2 | 6/2001 | |
| WO | WO 01/58360 A2 | 8/2001 | |
| WO | WO 02/11621 A1 | 2/2002 | |
| WO | WO 02/34122 A2 | 5/2002 | |
| WO | WO 02/094082 A2 | 11/2002 | |
| WO | WO 03/045260 A1 | 6/2003 | |
| WO | WO 03/047684 A2 | 6/2003 | |
| WO | WO 03/059412 A2 | 7/2003 | |
| WO | WO 03/078721 A2 | 9/2003 | |
| WO | WO 03/081761 A2 | 10/2003 | |
| WO | WO 03/082129 A2 | 10/2003 | |
| WO | WO 2004/006789 A1 | 1/2004 | |
| WO | WO 2004/028613 A2 | 4/2004 | |
| WO | WO 2004/037123 A1 | 5/2004 | |
| WO | WO 2004/037149 A1 | 5/2004 | |
| WO | WO 2004/052221 A1 | 6/2004 | |
| WO | WO 2004/086984 A1 | 10/2004 | |
| WO | WO 2005/009211 A2 | 2/2005 | |
| WO | WO 2005/018467 A2 | 3/2005 | |
| WO | WO 2005/037088 A2 | 4/2005 | |
| WO | WO 2005/048827 A1 | 6/2005 | |
| WO | WO 2005/065284 A2 | 7/2005 | |
| WO | WO 2005/097019 A2 | 10/2005 | |
| WO | WO 2005/097234 A2 | 10/2005 | |
| WO | WO 2005/112810 A2 | 12/2005 | |
| WO | WO 2005/120363 A1 | 12/2005 | |
| WO | WO 2006/007399 A1 | 1/2006 | |
| WO | WO 2006/012630 A2 | 2/2006 | |
| WO | WO 2006/040109 A1 | 4/2006 | |
| WO | WO 2006/041881 A2 | 4/2006 | |
| WO | WO 2006/060405 A2 | 6/2006 | |
| WO | WO 2006/110733 A2 | 10/2006 | |
| WO | WO 2006/113216 A2 | 10/2006 | |
| WO | WO 2007/013059 A2 | 2/2007 | |
| WO | WO 2007/014063 A2 | 2/2007 | |
| WO | WO 2007/048085 A2 | 4/2007 | |
| WO | WO 2007/063550 A2 | 6/2007 | |
| WO | WO 2007/100067 A1 | 9/2007 | |
| WO | WO 2007/109171 A2 | 9/2007 | |
| WO | WO 2008/005433 A1 | 1/2008 | |
| WO | WO 2008/033356 A2 | 3/2008 | |
| WO | WO 2008/041225 A2 | 4/2008 | |
| WO | WO 2008/076337 A1 | 6/2008 | |
| WO | WO 2008/076800 A2 | 6/2008 | |
| WO | WO 2008/079440 A2 | 7/2008 | |
| WO | WO 2008/101075 A2 | 8/2008 | |
| WO | WO 2008/102154 A2 | 8/2008 | |
| WO | WO 2008/108863 A2 | 9/2008 | |
| WO | WO 2008/151237 A1 | 12/2008 | |
| WO | WO 2009/021030 A1 | 2/2009 | |
| WO | WO 2009/027065 A1 | 3/2009 | |
| WO | WO 2009/029065 A1 | 3/2009 | |
| WO | WO 2009/032623 A2 | 3/2009 | |
| WO | WO 2009/121017 A1 | 10/2009 | |
| WO | WO 2010/027688 A1 | 3/2010 | |
| WO | WO 2010/080974 A1 | 7/2010 | |
| WO | WO 2010/088481 A1 | 8/2010 | |

OTHER PUBLICATIONS

U.S. Appl. No. 11/706,766, filed Feb. 15, 2007.
U.S. Appl. No. 11/706,811, filed Feb. 15, 2007.
U.S. Appl. No. 11/707,831, filed Feb. 16, 2007.
U.S. Appl. No. 11/715,710, filed Mar. 8, 2007.
U.S. Appl. No. 11/744,271, filed May 4, 2007.
U.S. Appl. No. 11/744,279, filed May 4, 2007.
U.S. Appl. No. 11/796,035, filed Apr. 26, 2007.
U.S. Appl. No. 11/796,357, filed Apr. 27, 2007.
U.S. Appl. No. 11/894,358, filed Aug. 21, 2007.
U.S. Appl. No. 11/897,676, filed Aug. 31, 2007.
U.S. Appl. No. 11/968,810, filed Jan. 3, 2008.
U.S. Appl. No. 11/981,070, filed Oct. 31, 2007.
U.S. Appl. No. 11/981,078, filed Oct. 31, 2007.
U.S. Appl. No. 11/981,134, filed Oct. 31, 2007.
U.S. Appl. No. 11/986,084, filed Nov. 20, 2007.
U.S. Appl. No. 11/986,420, filed Nov. 21, 2007.
U.S. Appl. No. 11/986,489, filed Nov. 21, 2007.
U.S. Appl. No. 11/998,370, filed Nov. 29, 2007.
U.S. Appl. No. 12/014,417, filed Jan. 5, 2008.
U.S. Appl. No. 12/019,461, filed Jan. 24, 2008.
U.S. Appl. No. 12/109,673, filed Apr. 25, 2008.
U.S. Appl. No. 12/109,699, filed Apr. 25, 2008.
U.S. Appl. No. 12/115,916, filed May 6, 2008.
U.S. Appl. No. 12/122,031, filed May 16, 2008.
U.S. Appl. No. 12/129,784, filed May 30, 2008.
U.S. Appl. No. 12/129,880, filed May 30, 2008.
U.S. Appl. No. 12/130,010, filed May 30, 2008.
U.S. Appl. No. 12/130,023, filed May 30, 2008.
U.S. Appl. No. 12/130,224, filed May 30, 2008.
U.S. Appl. No. 12/130,652, filed May 30, 2008.
U.S. Appl. No. 12/133,109, filed Jun. 4, 2008.
U.S. Appl. No. 12/133,953, filed Jun. 5, 2008.
U.S. Appl. No. 12/163,255, filed Jun. 27, 2008.
U.S. Appl. No. 12/169,868, filed Jul. 9, 2008.
U.S. Appl. No. 12/170,862, filed Jul. 10, 2008.
U.S. Appl. No. 12/172,752, filed Jul. 14, 2008.
U.S. Appl. No. 12/172,766, filed Jul. 14, 2008.
U.S. Appl. No. 12/172,782, filed Jul. 14, 2008.
U.S. Appl. No. 11/762,855, filed Jun. 14, 2007.
Michael S. Kavic, M.D., "Natural Orifice Translumenal Endoscopic Surgery: "NOTES"", JSLS, vol. 10, pp. 133-134 (2006).
Ethicon, Inc., "Wound Closure Manual: Chapter 3 (The Surgical Needle)," 15 pages, (publication date unknown).
Guido M. Sclabas, M.D., et al., "Endoluminal Methods for Gastrotomy Closure in Natural Orifice TransEnteric Surgery (NOTES)," Surgical Innovation, vol. 13, No. 1, pp. 23-30, Mar. 2006.
Fritscher-Ravens, et al., "Transgastric Gastropexy and Hiatal Hernia Repair for GERD Under EUS Control: a Porcine Model," Gastrointestinal Endoscopy, vol. 59, No. 1, pp. 89-95, 2004.
Ogando, "Prototype Tools That Go With the Flow," Design News, 2 pages, Jul. 17, 2006.
Edd, et al., "In Vivo Results of a New Focal Tissue Ablation Technique: Irreversible Electroporation," IEEE Trans Biomed Eng, vol. 53, pp. 1409-1415, 2006.
Kennedy, et al., "High-Burst-Strength, Feedback-Controlled Bipolar Vessel Sealing," Surgical Endoscopy, vol. 12, pp. 876-878 (1998).
Collins et al., "Local Gene Therapy of Solid Tumors with GM-CSF and B7-1 Eradicates Both Treated and Distal Tumors," Cancer Gene Therapy, vol. 13, pp. 1061-1071 (2006).
K. Sumiyama et al., "Transesophageal Mediastinoscopy by Submucosal Endoscopy With Mucosal Flap Safety Value Technique," Gastrointest Endosc., Apr. 2007, vol. 65(4), pp. 679-683 (Abstract).
K. Sumiyama et al., "Submucosal Endoscopy with Mucosal Flap Safety Valve," Gastrointest Endosc. Apr. 2007, vol. 65(4) pp. 694-695 (Abstract).

K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).

"Z-Offset Technique Used in the Introduction of Trocar During Laparoscopic Surgery," M.S. Hershey NOTES Presentation to EES NOTES Development Team, Sep. 27, 2007.

USGI® EndoSurgical Operating System—g-Prox® Tissue Grasper/Approximation Device; [online] URL: http://www.usgimedical.com/eos/components-gprox.htm—accessed May 30, 2008 (2 pages).

Printout of web page—http://www.vacumed.com/zcom/product/Product.do?compid=27&prodid=852, #51XX Low-Cost Permanent Tubes 2MM ID, Smooth Interior Walls, VacuMed, Ventura, California, Accessed Jul. 24, 2007.

U.S. Appl. No. 11/706,460, filed Feb. 15, 2007.

U.S. Appl. No. 11/706,685, filed Feb. 15, 2007.

F.N. Denans, Nouveau Procede Pour La Guerison Des Plaies Des Intestines. Extrait Des Seances De La Societe Royale De Medecine De Marseille, Pendant Le Mois De Decembre 1825, et le Premier Tremestre De 1826, Séance Du 24 Fevrier 1826. Recueil De La Societe Royale De Medecin De Marseille. Marseille: Impr. D'Achard, 1826; 1:127-31. (with English translation).

I. Fraser, "An Historical Perspective on Mechanical Aids in Intestinal Anastamosis," Surg. Gynecol. Obstet. (Oct. 1982), vol. 155, pp. 566-574.

M.E. Ryan et al., "Endoscopic Intervention for Biliary Leaks After Laparoscopic Cholecystectomy: A Multicenter Review," Gastrointest. Endosc., vol. 47(3), 1998, pp. 261-266.

C. Cope, "Creation of Compression Gastroenterostomy by Means of the Oral, Percutaneous, or Surgical Introduction of Magnets: Feasibility Study in Swine," J. Vasc Intery Radiol, (1995), vol. 6(4), pp. 539-545.

J.W. Hazey et al., "Natural Orifice Transgastric Endoscopic Peritoneoscopy in Humans: Initial Clinical Trial," Surg Endosc, (Jan. 2008), vol. 22(1), pp. 16-20.

N. Chopita et al., "Endoscopic Gastroenteric Anastamosis Using Magnets," Endoscopy, (2005), vol. 37(4), pp. 313-317.

C. Cope et al., "Long Term Patency of Experimental Magnetic Compression Gastroenteric Anastamoses Achieved with Covered Stents," Gastrointest Endosc, (2001), vol. 53, pp. 780-784.

H. Okajima et al., "Magnet Compression Anastamosis for Bile Duct Stenosis After Duct to Duct Biliary Reconstruction in Living Donor Liver Transplantation," Liver Transplantation (2005), pp. 473-475.

A. Fritscher-Ravens et al., "Transluminal Endosurgery: Single Lumen Access Anastamotic Device for Flexible Endoscopy," Gastrointestinal Endosc, (2003), vol. 58(4), pp. 585-591.

G.A. Hallenbeck, M.D. et al., "An Instrument for Colorectal Anastomosis Without Sutrues," Dis col Rectum, (1963), vol. 5, pp. 98-101.

T. Hardy, Jr., M.D. et al., "A Biofragmentable Ring for Sutureless Bowel Anastomosis. An Experimental Study," Dis col Rectum, (1985), vol. 28, pp. 484-490.

P. O'Neill, M.D. et al., "Nonsuture Intestinal Anastomosis," Am J. Surg, (1962), vol. 104, pp. 761-767.

C.P. Swain, M.D. et al., "Anastomosis at Flexible Endoscopy: An Experimental Study of Compression Button Gastrojejunostomy," Gastrointest Endosc, (1991), vol. 37, pp. 628-632.

J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.

Endoscopic Retrograde Cholangiopancreatogram (ERCP); [online] URL: http://www.webmd.com/digestive-disorders/endoscopic-retrograde-cholangiopancreatogram-ercp.htm; last updated: Apr. 30, 2007; accessed: Feb. 21, 2008 (6 pages).

ERCP; Jackson Siegelbaum Gastroenterology; [online] URL: http://www.gicare.com/pated/epdgs20.htm; accessed Feb. 21, 2008 (3 pages).

D.G. Fong et al., "Transcolonic Ventral Wall Hernia Mesh Fixation in a Porcine Model," Endoscopy 2007; 39: 865-869.

B. Rubinsky, Ph.D., "Irreversible Electroporation in Medicine," Technology in Cancer Research and Treatment, vol. 6, No. 4, Aug. (2007), pp. 255-259.

D.B. Nelson, MD et al., "Endoscopic Hemostatic Devices," Gastrointestinal Endoscopy, vol. 54, No. 6, 2001, pp. 833-840.

CRE™ Pulmonary Balloon Dilator; [online] URL: http://www.bostonscientific.com/Device.bsci?page=HCP_Overview&navRe1Id=1000.1003&method=D..., accessed Jul. 18, 2008 (4 pages).

J.D. Paulson, M.D., et al., "Development of Flexible Culdoscopy," The Journal of the American Association of Gynecologic Laparoscopists, Nov. 1999, vol. 6, No. 4, pp. 487-490.

H. Seifert, et al., "Retroperitoneal Endoscopic Debridement for Infected Peripancreatic Necrosis," The Lancet, Research Letters, vol. 356, Aug. 19, 2000, pp. 653-655.

K.E. Mönkemüller, M.D., et al., "Transmural Drainage of Pancreatic Fluid Collections Without Electrocautery Using the Seldinger Technique," Gastrointestinal Endoscopy, vol. 48, No. 2, 1998, pp. 195-200, (Received Oct. 3, 1997; Accepted Mar. 31, 1998).

D. Wilhelm et al., "An Innovative, Safe and Sterile Sigmoid Access (ISSA) for NOTES," Endoscopy 2007, vol. 39, pp. 401-406.

Nakazawa et al., "Radiofrequency Ablation of Hepatocellular Carcinoma: Correlation Between Local Tumor Progression After Ablation and Ablative Margin," AJR, 188, pp. 480-488 (Feb. 2007).

Miklavčič et al., "A validated model of in vivo electric field distribution in tissues for electrochemotherapy and for DNA electrotransfer for gene therapy," Biochimica et Biophysica Acta, 1523, pp. 73-83 (2000).

Evans, "Ablative and cathether-delivered therapies for colorectal liver metastases (CRLM)," EJSO, 33, pp. S64-S75 (2007).

Wong et al., "Combined Percutaneous Radiofrequency Ablation and Ethanol Injection for Hepatocellular Carcinoma in High-Risk Locations," AJR, 190, pp. W187-W195 (2008).

Heller et al., "Electrically mediated plasmid DNA delivery to hepatocellular carcinomas in vivo," Gene Therapy, 7, pp. 826-829 (2000).

Widera et al., "Increased DNA Vaccine Delivery and Immunogenicity by Electroporation in Vivo," The Journal of Immunology, 164, pp. 4635-4640 (2000).

Weaver et al., "Theory of electroporation: A review," Bioelectrochemistry and Bioenergetics, 41, pp. 135-160 (1996).

Mulier et al., "Radiofrequency Ablation Versus Resection for Resectable Colorectal Liver Metastases: Time for a Randomized Trial?" Annals of Surgical Oncology, 15(1), pp. 144-157 (2008).

Link et al., "Regional Chemotherapy of Nonresectable Colorectal Liver Metastases with Mitoxanthrone, 5-Fluorouracil, Folinic Acid, and Mitomycin C May Prolong Survival," Cancer, 92, pp. 2746-2753 (2001).

Guyton et al., "Membrane Potentials and Action Potentials," W.B. Sanders, ed. Textbook of Medical Physiology, p. 56 (2000).

Guyton et al., "Contraction of Skeletal Muscle," Textbook of Medical Physiology, pp. 82-84 (2000).

"Ethicon Endo-Surgery Novel Investigational Notes and SSL Devices Featured in 15 Presentations at Sages," Apr. 22, 2009 Press Release; URL http://www.jnj.com/connect/news/a11/20090422_152000; accessed Aug. 28, 2009 (3 pages).

"Ethicon Endo-Surgery Studies Presented At DDW Demonstrate Potential of Pure NOTES Surgery With Company's Toolbox," Jun. 3, 2009 Press Release; URL http://www.jnj.com/connect/news/product/20090603_120000; accessed Aug. 28, 2009 (3 pages).

Castellvi et al., "Hybrid Transvaginal NOTES Sleeve Gastrectomy in a Porcine Model Using a Magnetically Anchored Camera and Novel Instrumentation," Abstract submitted along With Poster at SAGES Annual Meeting in Phoenix, AZ, Apr. 22, 2009 (1 page).

Castellvi et al., "Hybrid Transvaginal NOTES Sleeve Gastrectomy in a Porcine Model Using A Magnetically Anchored Camera and Novel Instrumentation," Poster submitted along with Abstract at SAGES Annual Meeting in Phoenix, AZ, Apr. 22, 2009 (1 page).

OCTO Port Modular Laparoscopy System for Single Incision Access, Jan. 4, 2010; URL http://www.medgadget.com/archives/2010/01/octo_port_modular_laparo...; accessed Jan. 5, 2010 (4 pages).

Hakko Retractors, obtained Aug. 25, 2009 (5 pages).

Zadno et al., "Linear Superelasticity in Cold-Worked NI-TI," Engineering Aspects of Shape Memory Alloys, pp. 414-419.

U.S. Appl. No. 12/607,252, filed Oct. 28, 2009.

U.S. Appl. No. 12/580,400, filed Oct. 16, 2009.
U.S. Appl. No. 12/607,388, filed Oct. 28, 2009.
U.S. Appl. No. 12/612,911, filed Nov. 5, 2009.
U.S. Appl. No. 12/614,143, filed Nov. 6, 2009.
U.S. Appl. No. 12/617,998, filed Nov. 13, 2009.
U.S. Appl. No. 12/640,440, filed Dec. 17, 2009.
U.S. Appl. No. 12/640,469, filed Dec. 17, 2009.
U.S. Appl. No. 12/640,476, filed Dec. 17, 2009.
U.S. Appl. No. 12/640,492, filed Dec. 17, 2009.
U.S. Appl. No. 12/641,823, filed Dec. 18, 2009.
U.S. Appl. No. 12/641,853, filed Dec. 18, 2009.
U.S. Appl. No. 12/641,837, filed Dec. 18, 2009.
U.S. Appl. No. 12/651,181, filed Dec. 31, 2009.
U.S. Appl. No. 12/696,598, filed Jan. 29, 2010.
U.S. Appl. No. 12/696,626, filed Jan. 29, 2010.
U.S. Appl. No. 12/752,701, filed Apr. 1, 2010.
U.S. Appl. No. 13/013,131, filed Jan. 25, 2011.
U.S. Appl. No. 13/013,147, filed Jan. 25, 2011.
U.S. Appl. No. 12/900,132, filed Oct. 7, 2010.
U.S. Appl. No. 12/939,441, filed Nov. 4, 2010.
U.S. Appl. No. 12/902,531, filed Oct. 12, 2010.
U.S. Appl. No. 12/902,550, filed Oct. 12, 2010.
Zadno et al., "Linear Superelasticity in Cold-Worked NI-TI," Engineering Aspects of Shape Memory Alloys, pp. 414-419 (1990).
How Stuff Works "How Smart Structures Will Work," http://science.howstuffworks.com/engineering/structural/smart-structure1.htm; accessed online Nov. 1, 2011 (3 pages).
Instant Armor: Science Videos—Science News—ScienCentral; http://www.sciencentral.com/articles./view.php3?article_id=218392121; accessed online Nov. 1, 2011 (2 pages).
Stanway, Smart Fluids: Current and Future Developments. Material Science and Technology, 20, pp. 931-939, 2004; accessed online Nov. 1, 2011 at http://www.dynamics.group.shef.ac.uk/smart/smart.html (7 pages).
Jolly et al., Properties and Applications of Commercial Magnetorheological Fluids. SPIE 5th Annual Int. Symposium on Smart Structures and Materials, 1998 (18 pages).
U.S. Appl. No. 13/036,895, filed Feb. 28, 2011.
U.S. Appl. No. 13/036,908, filed Feb. 28, 2011.
U.S. Appl. No. 13/267,251, filed Oct. 6, 2011.
U.S. Appl. No. 13/325,791, filed Dec. 14, 2011.
U.S. Appl. No. 13/352,495, filed Jan. 18, 2012.
U.S. Appl. No. 13/399,358, filed Feb. 17, 2012.
U.S. Appl. No. 13/420,805, filed Mar. 15, 2012.
U.S. Appl. No. 13/420,818, filed Mar. 15, 2012.
U.S. Appl. No. 13/425,103, filed Mar. 20, 2012.

* cited by examiner

ANASTOMOTIC DEVICE

BACKGROUND

The various embodiments relate generally to surgical devices for forming an anastomosis between organs, and more particularly, to devices that can be inserted through a natural orifice in the body and used to form an anastomosis between various gastrointestinal organs.

Access to the abdominal cavity may be required, from time to time, for diagnostic and therapeutic endeavors for a variety of medical and surgical procedures. Historically, abdominal access has required a formal laparotomy, e.g., abdominal surgery through a surgical incision made in the wall of the abdomen to provide adequate exposure. Such procedures, however, require incisions to be made in the abdomen and may not be particularly well-suited for patients having extensive abdominal scarring from previous procedures, persons who are morbidly obese, individuals with abdominal wall infection, and patients with diminished abdominal wall integrity, such as patients with burns and skin grafting. Other patients simply do not want to have a scar if it can be avoided.

Such conventional open surgical procedures also are employed to address various problems occurring in the gastrointestinal tract, such as the stomach, duodenum, bile duct, jejunum (a portion of the small intestine), colon, ileum, or bowels. Surgical procedures in the gastrointestinal tract are generally performed to treat obese patients, e.g., to decrease absorption of nutrients, and to treat blockages, obstructions, or strictures in the gastrointestinal tact. Blockages, obstructions, or strictures may occur in the duodenum, bile duct, jejunum, or bowels from disease processes such as malignant or benign cancers or tumors and may be treated by using stents or creating an anastomosis between organs in the gastrointestinal tract.

Conventional surgical procedures are employed to insert stents within a blocked, obstructed, or narrowed viscus to provide palliative relief. The stents are located within the viscus to restore or provide some degree of drainage of fluid through the blocked, obstructed, or narrowed viscus. A limitation of stents is the tendency of occlusion and cholangitis resulting from the development of bacterial biofilm. Plastic stents provide a relatively narrow luminal size and therefore lead to a high occlusion rate. Metal expandable stents, despite having significantly increased patency and longer life than plastic stents, also are prone to occlusion and are extremely expensive. Stents may be located within the bile duct, for example, to provide palliative relief of obstructive jaundice resulting from blockages occurring in the bile duct. Rather than stenting the obstruction, creating a permanent fistula of larger diameter than the bile duct between the bile duct and the duodenum provides greater drainage of bile. Therefore, there is a need to provide a new method and apparatus for forming a biliary duodenal anastomosis. There is also a need for a new method and apparatus for forming a biliary drainage anastomosis by forming a choledochoduodenostomy above the ampulla.

Anastomosis is the joining of luminal structures within the body by way of collateral channels when the natural channels are blocked. Common examples are colonic anastomosis in which two portions of the colon are joined together. The anastomosis may be formed between various organs in the gastrointestinal tract. A gastro-jejunostomy anastomosis may be created between the stomach and the jejunum to treat blockages in the duodenum or for malabsorption, e.g., gastric bypass surgery. An entero-enteral anastomosis may be created for jejuno-jeunal bariatric purposes, a colon to ileum anastomosis may be created for bypassing colorectal cancer, and a biliary duodenal anastomosis may be created between the bile duct and the duodenum above a malignant or benign obstruction in the bile duct. Some anastomoses are created using compression techniques. Certain procedures also may require large openings in the bowel wall. Anastomoses also may be formed using linear staplers and require two large centimeter sized holes to be formed in the patient. Thus, most gastrointestinal anastomoses are created using open surgical procedures requiring the patient to be placed under general anesthesia and large incisions in the abdominal wall. Attendant disadvantages of such open surgical procedures include the necessity for general anesthesia, increased post-operative pain, intra-abdominal adhesions, as well as in-patient hospitalization with associated inconvenience and costs.

Some anastomoses may be created by compression or sutureless techniques. A compression anastomosis is formed by necrotic ischemia caused by the occlusion of the blood supply to the tissue. Compression is applied to the tissue using one or more masses to sandwich the tissue in the target area. One compression anastomosis technique employs a compression button that erodes through the bowel wall over several days because of ischemic necrosis resulting in a leak free anastomosis. Another sutureless compression anastomosis technique employs a bio-fragmentable ring to create an anastomosis in the bowel. This technique compared favorably to sutured and stapled anastomosis. Other anastomoses may be created using flexible endoscopy techniques employing spring compression buttons. Flexible endoscopy anastomosis techniques may employ ultrasonography techniques when access is limited to a single endoscopic lumen. Magnets also have been used to form compression anastomoses when access is possible to both transgastric lumens or by passing a device through the jejunum. Magnetic compression gastroenteric anastomosis may be performed by introducing magnets perorally with endoscopic and fluoroscopic guidance and mated across the gastric and jejunal walls. Compression anastomosis may be formed between bile ducts using magnets following duct stenosis in liver transplant patients. In addition to suffering from the limitations discussed above, current open, laparoscopic, and endoscopic surgical techniques fail to provide a convenient way for inserting a distal mass into the gastrointestinal tract and are generally incapable of applying sufficient mass and force to accomplish a clinically acceptable compression anastomosis.

Therefore, there is a need for an alternative to conventional surgery that eliminates abdominal incisions and incision-related complications to diagnose and treat abdominal pathology. There is a need for a new method and apparatus for forming a compression anastomosis. Also, there is a need for a surgical method and apparatus for forming an anastomosis between luminal structures or organs using a minimally invasive surgical technique. More particularly, there is a need for a surgical apparatus for forming anastomosis between various gastrointestinal organs that can be inserted through a natural orifice in the body using a minimally invasive surgical technique. Further, there is a need for a surgical apparatus that can be introduced into the stomach through the mouth for creating clinically acceptable compression anastomosis between the stomach and the jejunum, the colon and the ileum, and/or the bile duct and the duodenum (e.g., biliary-duodenal anastomosis) using minimally invasive surgical techniques. The foregoing discussion is intended only to illustrate some of the shortcomings present in the field at the time, and should not be taken as a disavowal of claim scope.

SUMMARY

In one embodiment, an apparatus includes an anastomotic portion comprising a first end and a second end. At least one flexible portion protrudes from the first end of the anastomotic portion. The at least one flexible portion comprises a first articulation node located at a predetermined distance from the first end of the anastomotic portion. The articulation node enables the at least one flexible portion to move relative to the anastomotic portion.

FIGURES

The novel features of the various embodiments are set forth with particularity in the appended claims. The various embodiments, however, both as to organization and methods of operation, together with advantages thereof, may best be understood by reference to the following description, taken in conjunction with the accompanying drawings as follows.

DESCRIPTION

Figure 1:
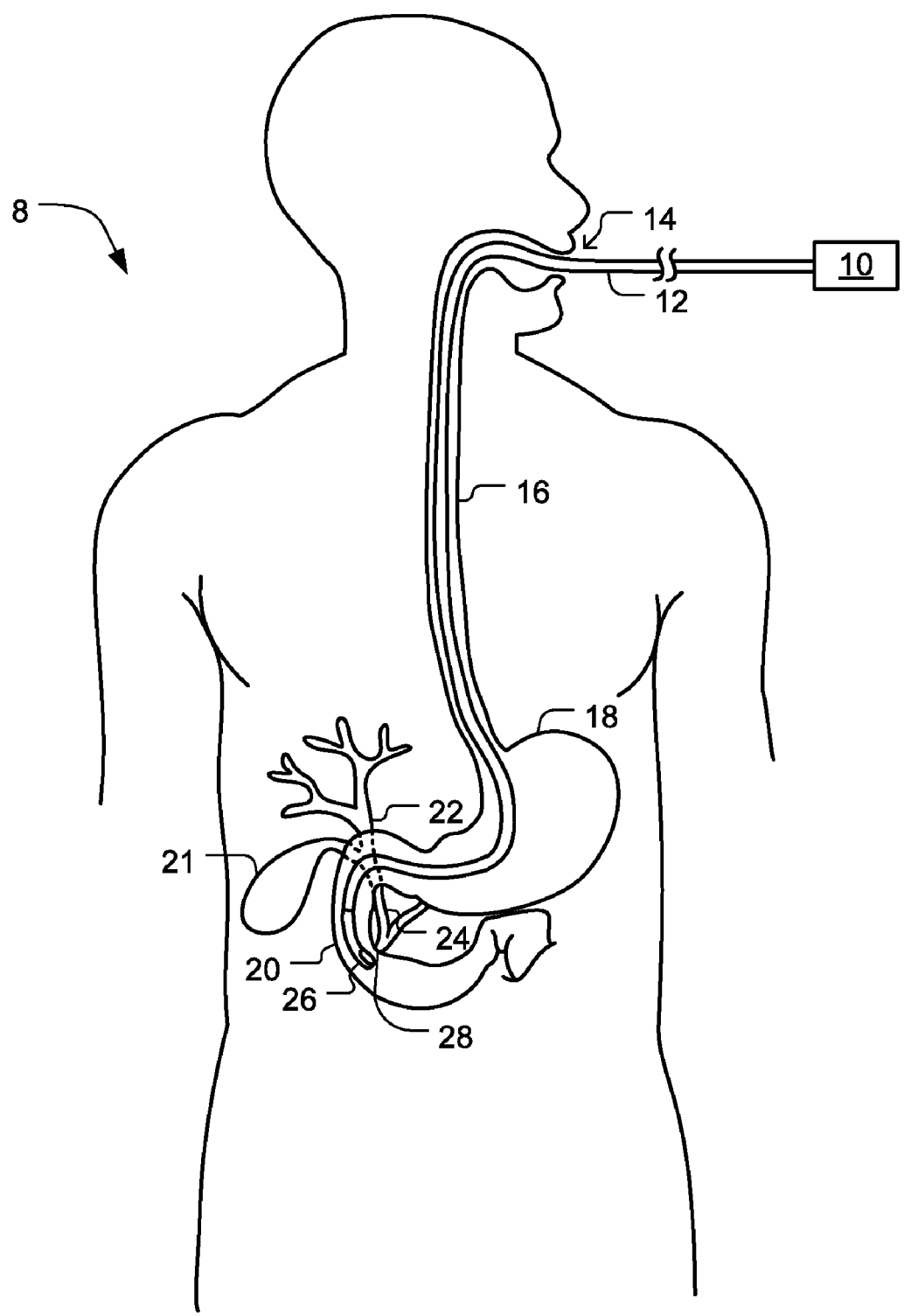
FIG. 1 is a diagrammatical view illustrating one embodiment of a minimally invasive surgical device introduced into a natural opening of a patient.

Various embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting embodiments and that the scope of the various embodiments is defined solely by the claims. The features illustrated or described in connection with one embodiment may be combined with the features of other embodiments. Such modifications and variations are intended to be included within the scope of the claims.

It will be appreciated that the terms "proximal" and "distal" are used herein with reference to a clinician manipulating an end of an instrument that protrudes out of the mouth of the patient. The term "proximal" refers to the portion closest to the surgeon and the term "distal" refers to the portion located away from the surgeon. It will be further appreciated that for conciseness and clarity, spatial terms such as "vertical," "horizontal," "up," and "down" may be used herein with respect to the drawings. However, surgical instruments are used in many orientations and positions, and these terms are not intended to be limiting and absolute.

The various embodiments generally provide methods and devices for creating anastomosis at various sites, e.g., target areas or tissue treatment regions, in the gastrointestinal tract. The devices may be introduced via natural orifices and may be combined with trans-organ techniques. In one embodiment, a Natural Orifice Translumenal Endoscopic Surgery (NOTES)™ techniques may be employed to introduce instruments into the patient and carry out the various procedures described hereinbelow. A NOTES™ technique is a minimally invasive therapeutic procedure that may be employed to treat diseased tissue through a natural opening of the patient without making incisions in the abdomen. A natural opening may be the mouth, anus, and/or vagina. Medical implantable instruments may be introduced into the patient to the target area via the natural opening. In a NOTES™ technique, a surgeon inserts a flexible endoscope into one or more natural openings of the patient to view the target area using a camera. During endoscopic surgery the surgeon inserts surgical devices through one or more lumens or working channels of the endoscope to perform various key surgical activities (KSA). These KSAs include forming an anastomosis between organs, and more particularly, forming anastomosis between gastrointestinal organs with devices that can be inserted through a natural opening of the body.

Although various embodiments described herein refer to for creating an anastomosis between the duodenum and the bile duct by accessing those organs through the mouth and esophagus of a patient, those of ordinary skill in the art will readily appreciate that unique and novel aspects of the various embodiments could be successfully employed in connection with forming anastomosis between other organs by gaining access thereto through other natural openings such as the anus, or the vagina, for example, without departing from the scope of the appended claims.

FIG. 1 is a diagrammatical view illustrating one embodiment of a minimally invasive surgical device introduced into a natural opening of a patient. In the illustrated embodiment, an endoscope 10 comprising a flexible shaft 12 is introduced into the mouth 14, though the esophagus 16, and into the stomach 18 of a patient 8. The flexible shaft 12 may be passed through a per-oral overtube (a plastic tube of varying length) to protect the esophagus 16 when the flexible shaft 12 of the endoscope 10 is introduced into the patient 8. From the stomach 18, a distal end 26 of the flexible shaft 12 of the endoscope 10 is inserted in the duodenum 20. From the duodenum 20, an anastomotic device may be introduced into a portion of the biliary tree 22 through the sphincter of Oddy ampullary opening 28. In one embodiment, the endoscope 10 may be a side-viewing or front-viewing endoscope. In one embodiment, the endoscope 10 could be used in an endoscopic retrograde cholangio-pancreatography (ERCP) technique to access and image the bile duct 24 endoscopically. In an ERCP technique, a catheter is introduced through the opening 28 of the bile duct 24 from the duodenum 20 via a working channel of a side-viewing flexible ERCP endoscope 10 under X-Ray or fluoroscopic guidance.

Figure 2:
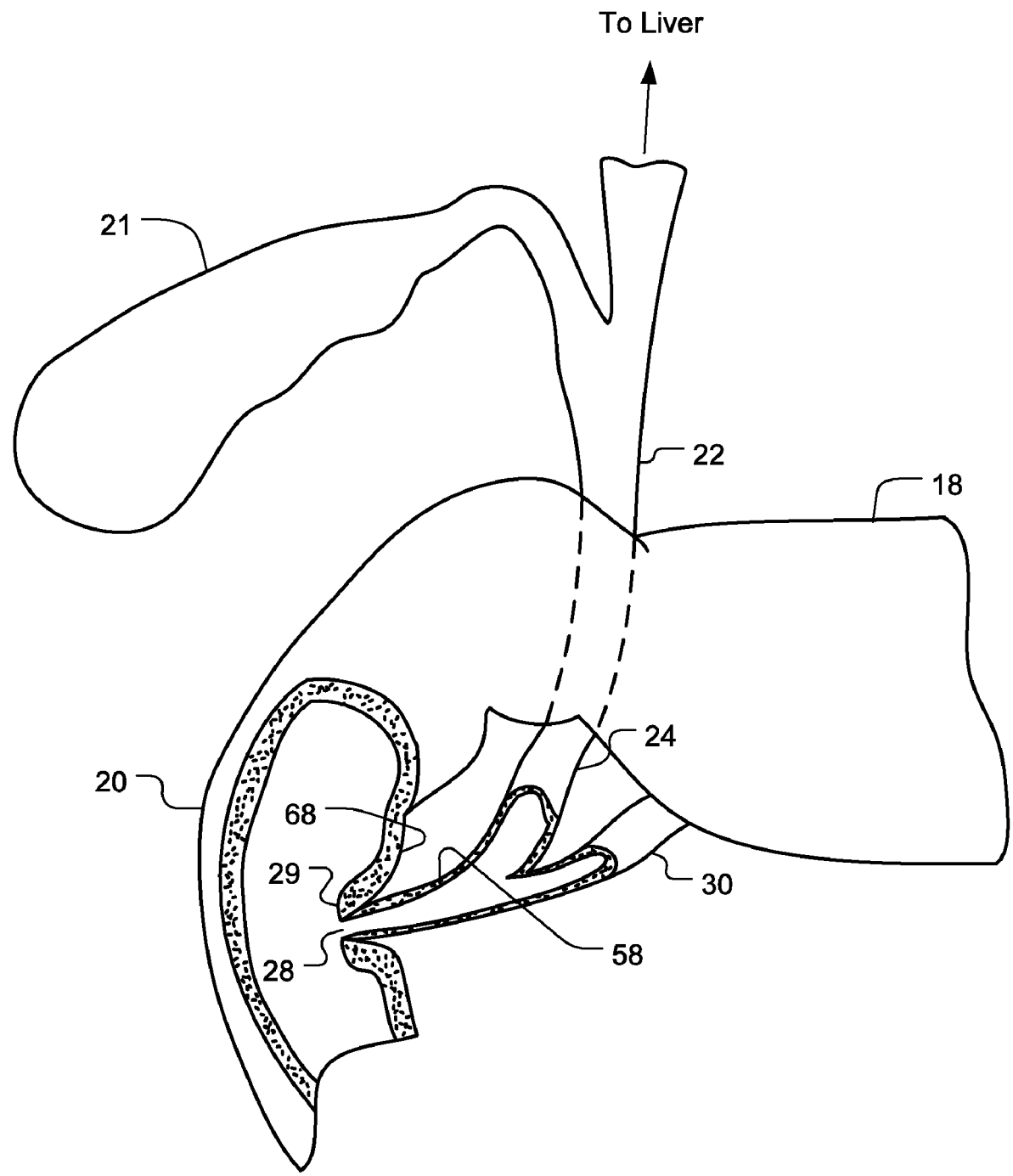
FIG. 2 illustrates a partial cross-sectional view of the duodenum, the bile duct, and the pancreatic duct.

FIG. 2 illustrates a partial cross-sectional view of the duodenum 20, the bile duct 24, and the pancreatic duct 30. The biliary tree 22 connects the gall bladder 21 and the liver (not shown) to the duodenum 20 through the opening 28. The bile duct 24 and the pancreatic duct 30 enter the descending duodenum 20, commonly known together as the hepatopancreatic duct (or pancreatic duct), through the major duodenal papilla 29 and the common orifice 28. The bile duct 24 and the pancreatic duct 30 are in fluid communication with the duodenum 20 through the common opening 28. An anastomotic device may be introduced into the bile duct 24 through the opening 28 after cannulation of the bile duct 24 with the distal end 26 of the endoscope 10. Biliary cannulation and placement of an anastomotic device may be accomplished with both standard forward viewing and side-viewing endoscopes, for example.

Figure 3:
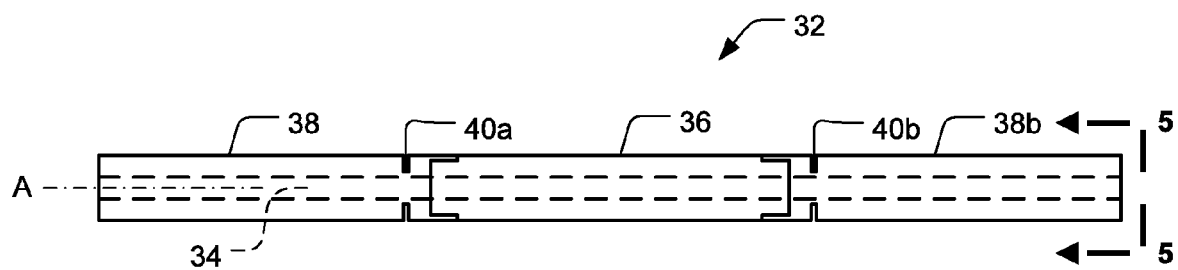
FIG. 3 illustrates one embodiment of an apparatus for forming a compression anastomosis.
Figure 4:
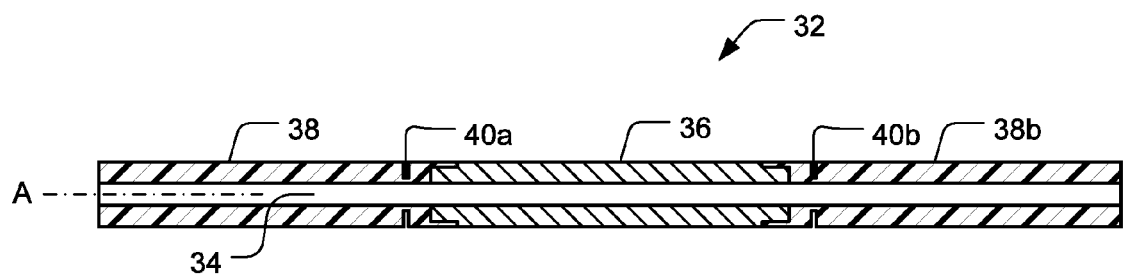
FIG. 4 is a cross-sectional view of one embodiment of an apparatus for forming a compression anastomosis.
Figure 5:
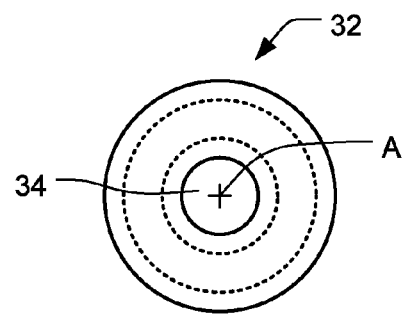
FIG. 5 is an end view of one embodiment of an apparatus for forming a compression anastomosis taken along line 5-5 as shown in FIG. 3.

FIGS. 3-5 illustrate one embodiment of an apparatus for forming a compression anastomosis. In the illustrated embodiment, an anastomotic device 32 comprises a general longitudinal tubular structure suitable for positioning within a hollow viscus to drain fluid through a central lumen to palliate an obstruction within the hollow viscus. The anastomotic device 32 may be introduced into a hollow viscus using a flexible endoscope over a guide-wire and can be pushed into position with a catheter or pusher tube. In one embodiment, the anastomotic device 32 is shaped like a thin flexible catheter that can be inserted into the hollow viscus requiring anastomosis. The positioning of the anastomotic device 32 may be conducted under direct vision with an endoscope. The anastomotic device 32 may be introduced into the hollow viscus of the bile duct 24 through the opening 28 after the bile duct 24 is cannulated with the distal end 26 of the endoscope 10. Once positioned in the bile duct 24, the anastomotic device 32 performs the function of a biliary stent to palliate a blockage, obstruction, or stricture in the bile duct 24. The anastomotic device 32 also comprises articulation nodes that enable flexible portions of the anastomotic device 32 to move relative to other more rigid portions of the anastomotic device 32. When the flexible portions of the anastomotic device 32 are in flexion, the anastomotic device 32 can pass through the anastomosis once it is formed.

In one embodiment, the anastomotic device 32 comprises a first portion 36 having a first and second end. In one embodiment, at least a first flexible portion 38a protrudes from one end. In another embodiment, the anastomotic device 32 may comprise a second flexible portion 38b protruding from the other end. The first portion 36 is generally substantially rigid relative to the first and second flexible portions 38a, b, although in some embodiments, the first portion 36 may be formed of flexible materials. In one embodiment, the first and second flexible portions 38a, b may be fastened, linked, associate together, joined, connected, or attached to the first portion 36. In another embodiment, the first and second flexible portions 38a, b may be formed integrally with the first portion 36 as a continuous component. For conciseness and clarity, the first portion 36 is referred to herein as the anastomotic portion 36. The anastomotic portion 36 comprises an anastomotic surface, which is defined as the portion of the anastomotic device 32 that contacts one side of the tissue to be anastomosed. In the illustrated embodiment, the anastomotic portion 36 is in fluid communication with the first flexible portion 38a on one end and is in fluid communication with the second flexible portion 38b on the other end. In other words, in one embodiment, the anastomotic portion 36 is located between the first and second flexible portions 38a, b and the three portions are in fluid communication by way of a central lumen 34 for conducting fluid. In the illustrated embodiment, the anastomotic portion 36 and the first and second flexible portions 38a, b have a generally cylindrical form with the central lumen 34 fluidically coupling the three portions to conduct fluid therethrough. In one embodiment, the central lumen 34 may be eliminated and the anastomotic device 32 may be comprised of a solid material. This embodiment may be employed in applications that do not require fluid to be drained through the anastomotic device 32.

In one embodiment, the anastomotic portion 36 may be formed of any one of a ferrous, magnetic, or paramagnetic material. It will be appreciated by those skilled in the art that paramagnetism is a form of magnetism which occurs only in the presence of an externally applied magnetic field. Accordingly, paramagnetic materials are attracted to magnetic fields, and hence have a relative magnetic permeability greater than one (or, equivalently, a positive magnetic susceptibility). In other embodiments, the anastomotic portion 36 may comprise magnets or magnetic material attached thereto. In other embodiments, the anastomotic portion 36 may be formed of non-ferrous material having magnets formed integral therewith or attached thereto. In various other embodiments, the anastomotic portion 36 may be formed of ferrous, magnetic, or paramagnetic material. In various embodiments, the anastomotic portion 36 may be formed of quaternary Iron, Neodymium, Iron, Boron, and/or Samarium materials. In one embodiment, the anastomotic portion 36 may be encased in a protective plastic. In one embodiment, the anastomotic portion 36 may comprise a coating such as plated Chromium. In one embodiment, the first portion 36 also may be formed of rubber plastic magnetic strips which may be flexible. In various embodiments, the rubber magnetic strips may be formed by incorporating Neodymium, Iron, and/or Boron particles in a rubber or plastic material.

In one embodiment, the first and second flexible portions 38a, b are formed of flexible tubular plastic material. The plastic tubes may be formed of a polymeric material such as polyethylene. The first and second flexible portions 38a, b may be tapered or untapered. In one embodiment, the flexible portions 38a, b may be tapered towards the free end to aid introduction of the anastomotic device 32 into the hollow viscus. In one embodiment, a conical element may be attached to either one or both of the first and second plastic portions 38a, b to assist introduction of the anastomotic device 32 in a narrow opening. The conical element may comprise a lumen to conduct fluid therethrough. In one embodiment, the first and second flexible portions 38a, b may be hollow plastic tubes or may be a solid material.

Each of the first and second flexible portions 38a, b comprise articulation nodes 40a, b situated at some distance from either end of the anastomotic portion 36. Each of the articulation nodes 40a, b forms a movable joint between the anastomotic portion 36 and each of the flexible portions 38a, b. One or both of the flexible portions 38a, b may comprise the articulation nodes 40a, b to enable the flexible portions 38a, b of the anastomotic device 32 to move relative to the anastomotic portion 36 and allowing a limited angle of rotation between the anastomotic portion 36 and the flexible portions 38a, b. The articulation nodes 40a, b enable the flexible portions 38a, b to move (e.g., flex, rotate over a limited angle, fold, bend, buckle, collapse, deform, or otherwise change shape) relative to the anastomotic portion 36. For example, the articulation nodes 40a, b enable the flexible portions 38a, b to move from a continuous longitudinally extending tube to a "U-shaped" tube. In flexion, the anastomotic device 32 can fall through the anastomosis. In the illustrated embodiment, the articulation nodes 40a, b are formed as weaknesses on the flexible portions 38a, b. The substantially elongated tubular first and second flexible portions 38a, b bend, collapse, or deform at the articulation nodes 40a, b when the anastomotic portion 36 is magnetically coupled to a larger mass to enable the anastomotic device 32 to fall through a mature anastomosis toward the side having a larger mass. In the embodiments illustrated in FIGS. 15-26, for example, the articulation nodes 40a, b form a collapsible biliary anastomotic device 32 to create a compression anastomosis between the biliary tree 22 and the duodenum 20. The first and second flexible portions 38a, b begin to move as the anastomosis matures and the anastomotic portion 36 is magnetically attracted to a larger mass and falls through the compression anastomosis leaving a fistula above the papilla 29. In other embodiments, the articulation nodes 40a, b may be formed such that the flexible portions 38a, b fall apart or release from the anastomotic portion 36 after the anastomotic device 32 is positioned within the hollow viscus, e.g., the bile duct 24.

In the illustrated embodiment, the central lumen 34 extends along a longitudinal axis A. The central lumen 34 is suitable for conducting fluid within the hollow viscus during the period required for the translumenal anastomosis to mature. For example, in one application, the anastomotic device 32 may be positioned in the bile duct 24 across an area of obstruction to form a biliary duodenal anastomosis. While the anastomosis matures (generally a few days), the central lumen 34 drains bile from the bile duct 24 to the duodenum 20.

The anastomotic device 32 also may comprise serrations to retain the anastomotic device 32 positioned within the hollow viscus to minimize the opportunity of the anastomotic device 32 falling out of the hollow viscus. The serrations also may serve to control how far the anastomotic device 32 can be introduced into the hollow viscus. In one embodiment, the anastomotic device 32 may comprise a proximal thread, which can be grasped with a clamp-like end effect or introduced through the working channel of the endoscope 10, to retract the anastomotic device 32 in case it is pushed too far within the hollow viscus.

Figure 6:
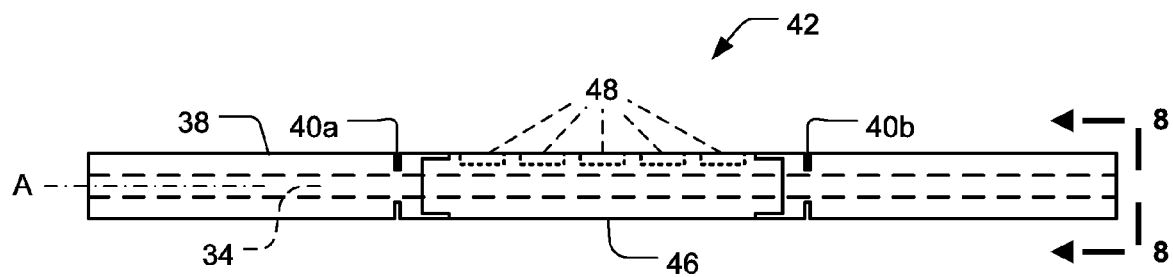
FIG. 6 illustrates one embodiment of an apparatus for forming a compression anastomosis.
Figure 7:
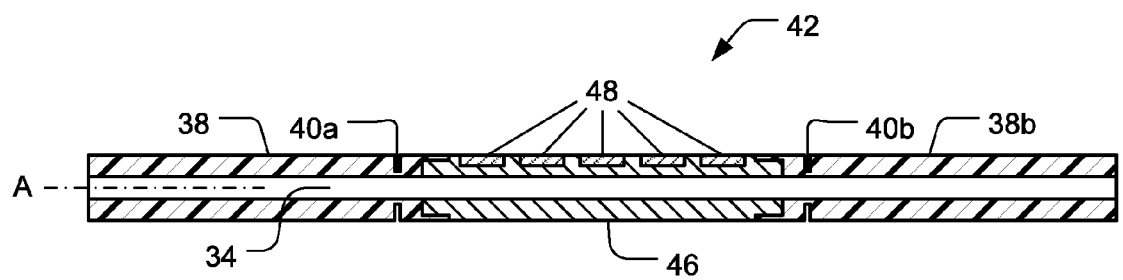
FIG. 7 is a cross-sectional view of one embodiment of an apparatus for forming a compression anastomosis.
Figure 8:
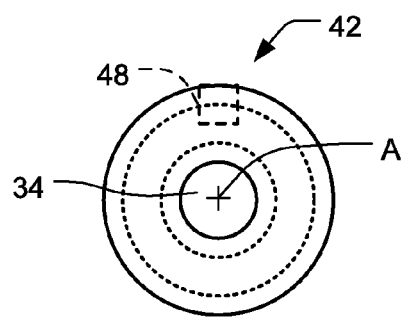
FIG. 8 is an end view of one embodiment of an apparatus for forming a compression anastomosis taken along line 8-8 as shown in FIG. 6.

FIGS. 6-8 illustrate one embodiment of a surgical instrument for forming a compression anastomosis. In the illustrated embodiment, an anastomotic device 42 comprises at least one anastomotic portion 46 and the at least one flexible portion 38a. The anastomotic portion 46 may be formed of ferrous or non-ferrous materials and may comprise at least one magnet 48 attached thereto. In the illustrated embodiment, the anastomotic portion 46 comprises a plurality of magnets 48 and is sandwiched between the first and second flexible portions 38a, b as described above with reference to FIGS. 3-5. In one embodiment, the magnets 48 may be discrete magnets embedded and spaced apart in plastic to allow the anastomotic portion 46 to bend to a certain degree. In various embodiments, the anastomotic portion 46 also may be formed of magnetic flexible rubber plastic strips, which may be formed by incorporating Neodymium, Iron, and/or Boron particles in a rubber or plastic material.

In various embodiments, the anastomotic devices 32, 42 may comprise a guide-wire running through the central lumen 34, a second lumen formed through the body portions of the anastomotic devices 32, 42 (e.g., the anastomotic portion 36, the anastomotic portion 46, and the first and second portions 38a, b), or in a tract along the outside the anastomotic devices 32, 42. In one embodiment, the anastomotic devices 32, 42 also may comprise a guide-wire along a portion of its length exiting on the side in a monorail configuration. In one embodiment, the ends of the anastomotic devices 32, 42 may be straight or curled (pigtail) in shape. In one embodiment the anastomotic device 32, 42 also could be impregnated with a drug, for example a chemotherapeutic drug, which could be placed in an obstructed viscus, e.g., a bile duct obstructed from biliary or pancreatic cancer, and deliver treatment to the tumor for several days while the anastomosis is forming. In one embodiment, the anastomotic devices 32, 42 also could be radioactive and be used for treating the tumors of the gastrointestinal tract. In one embodiment, the anastomotic devices 32, 42 also could be biodegradable and reduce the possibility of the magnet and/or anastomotic device 32, 42 assembly getting stuck in the gastrointestinal tract.

In one embodiment, the anastomotic device 32, 42 may be placed across a tumor and magnetic "seeds" embedded with a chemotherapeutic or radioactive material may be employed to deliver drug or radiation to the tumor. A magnet 50, 60

(FIGS. 9-14) may be subsequently located in the stomach 18 or bowel to form an anastomosis.

The anastomotic devices 32, 42 may be employed in combination with an external mass, e.g., magnets 50, 60 (FIGS. 9-14), to form a compression anastomosis at a wide range of target areas. The combination of the anastomotic device 32, 42 and the magnet 50, 60 is referred to herein as a magnet assembly 86 (FIGS. 20-26). In the embodiment illustrated in FIGS. 21, 22, and 24-26, an anastomosis 84 is formed by coupling the anastomotic device 42 with the magnet 50 to compress tissue above the ampullary opening 28 between the duodenum 20 and the bile duct 24. In one embodiment, the combination of the anastomotic device 32, 42 and the magnet 50, 60, e.g., the magnet assembly 86, may be employed to form anastomosis using a variety of surgical techniques including, for example, a NOTES™ procedure, a laparoscopy, a or laparotomy. The types of anastomosis that may be formed using the magnet assembly 86 comprised of any combination of the anastomotic devices 32, 42 and the magnets 50, 60 include entero-enteral anastomoses to treat blockages in the bile duct, jejuno-jeunal anastomoses for bariatric purposes, and/or colon to ileum anastomoses for bypassing colorectal cancer, among others. The magnet assembly 86 also may be employed to form biliary duodenal anastomoses between the bile duct 24 and the duodenum 20 above malignant or benign obstructions. The magnet assembly 86 can form anastomoses with a diameter that is much larger than the diameter of a conventional stent. A compression anastomosis formed of epithelialized tissue is not likely to result in a biofilm blockage, which is likely to occur with most conventional stents within a few weeks and thus will require replacement. In other embodiments, the magnet assembly 86 may be employed to form compression anastomoses without making large holes in the intestine. For example, the magnet assembly 86 may be employed to form two holes in the bowel that may be less than 3 mm in diameter. The magnet assembly 86 can be used with flexible instruments to form entero-enteral anastomosis having a length of about 3 mm to about 10 mm.

The magnetic compression magnet assembly 86 (FIGS. 20-26) also may be used to form anastomoses using an intralumenal endoscope (or radiological) to access the lumen of a first limb of an anastomosis and transgastric gastroscope to access the lumen of a second of the limb of the anastomosis. This may be accomplished by inserting the intralumenal endoscope in the rectum to access the first limb and inserting the transgastric gastroscope into the small intestine through a very small incision (e.g., keyhole, pinhole) and then pushing the gastroscope inside the intestine to connect with magnets held by the intralumenal endoscope. The magnet assembly 86 can be used with flexible instruments to form entero-enteral anastomosis using a double channel endoscope in a NOTES™ procedure.

Figure 9:
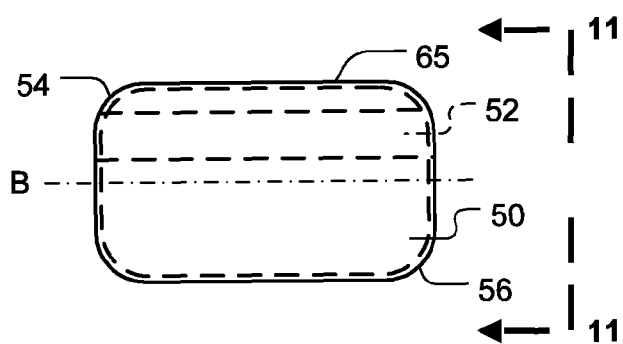
FIG. 9 illustrates one embodiment of a magnetic mass for forming a compression anastomosis.
Figure 11:
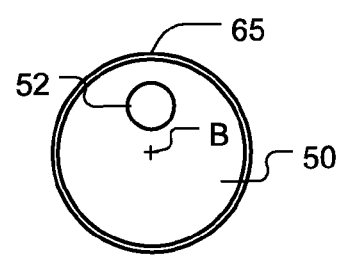
FIG. 11 is an end-view of one embodiment of a magnetic mass for forming a compression anastomosis taken along line 11-11 as shown in FIG. 9.
Figure 10:
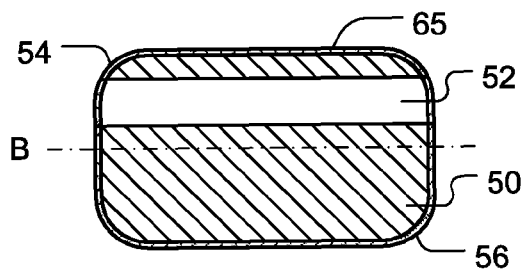
FIG. 10 is a cross-sectional view of one embodiment of a magnetic mass for forming a compression anastomosis.

FIGS. 9-11 illustrate one embodiment of a magnetic mass for forming a compression anastomosis. Employing a minimally invasive surgical technique, e.g., a NOTES™ procedure, the magnet 50 is introduced into a hollow organ or lumen adjacent to the target area where the anastomosis is to be formed. In one embodiment, the magnet 50 may be introduced into the lumen using an endoscope. In one embodiment, the magnet 50 is placed in the duodenum 20, for example, to work in conjunction with either one of the anastomotic device 32, 42 to form a biliary duodenal compression anastomosis. The magnet 50 is generally cylindrical in shape and may comprise a longitudinal lumen or opening 52. A guide-wire engages the opening 52 to locate the magnet 50 in the target area, e.g., the duodenum 20. In the embodiment illustrated in FIGS. 9-11, the opening 52 is offset from the central axis B. In the embodiment illustrated in FIGS. 12-14, the opening 52 may be centered about a central axis B. In one embodiment, the shape of the magnet 50 or its casing is capsular with radii 54, 56 formed on either end thereof. The rounded capsular geometry enables safe passage of the magnet 50 through the gastrointestinal tract. In one embodiment, the radii 54, 56 may have a substantially equal radius. In one embodiment, the magnet 50 may comprise a coating 65 such as plastic or plated in Chromium to resist corrosion in the body. The magnet 50 may be formed of Neodymium, Iron, Boron, and/or Samarium materials.

The strength of the magnet 50 should be sufficient to exert an attractive magnetic force to the anastomotic portion 36, 46 across the thickness of the tissue to be anastomosed. As an example, the tissue of the small intestine or colon is approximately 1 mm to 1.5 mm. Thus, in forming an anastomosis between the small intestine and the colon, the strength of the magnet 50 should be sufficient to exert an attractive magnetic force across tissue having a thickness of about 2 mm to about 3 mm. The strength of the magnet 50 should be suitable to exert a sufficient compressive force to tissue positioned (e.g., sandwiched) between the magnet 50 and the anastomotic portion 36, 46 to cause ischemic necrosis of the tissue. The compressive force generated by the magnetic attractive force on the tissue sandwiched between the magnet 50 and the anastomotic portion 36, 46 should be adequate to cause ischemic necrosis, fistulization, and the formation of an anastomosis therethrough. In one embodiment, the tissue compressed between the magnet 50 and the anastomotic portion 36, 46 may be a wall 58 of the bile duct 24 and a wall 68 of the duodenum 20 located just above the papilla 29 (FIGS. 15-26).

The polarities of the magnet 50 and the anastomotic portion 36, 46 should be oriented to create a suitable attractive magnetic force therebetween. In one embodiment, the anastomotic portion 36 and/or the magnet 50 may have markings indicative of the magnetic poles formed thereon to assist the user orient the devices. The magnet 50 and the anastomotic portion 36, 46 should be oriented to create a suitable attractive force between the magnet 50 and the anastomotic portion 36, 46 to line up and attract along the length of the desired anastomosis.

With reference now also to FIGS. 2-5, length of the magnet 50 should correspond substantially to the length of the anastomotic portion 36, 46 such that a suitable magnetic field develops therebetween to couple the two components substantially along the length of the anastomotic portion 36, 46 and the magnet 50. In one embodiment, the length of the magnet 50 may be the same as the length of the anastomotic portion 36, 46. In one embodiment, the magnet 50 and the anastomotic portion 36, 46 may be substantially similar.

In one embodiment, the magnet 50 may be formed as a single magnetic component. In other embodiments, the magnet 50 may comprise a stack of two or more hollow magnets preferably with a flexible tapered introducer. In one embodiment, the magnet 50 may be asymmetrical comprising more massive portions on a particular side to bias the way the combination of the magnet 50 and the anastomotic device 32, 42 falls through the anastomosis. For example, with the anastomotic device 32 located in the bile duct 24, it would be preferable to locate the more massive magnet 50 in the duodenum 20 to bias the anastomotic device 32 and urge it to pass from the wall 58 of the bile duct 24 through the wall 68 of the duodenum 20 and into jejunum and further into the small intestine. If a small intestinal colonic anastomosis is desired, it would be preferable to locate the anastomotic device 32, 42 in the small intestine and to locate a more massive magnet 50 in the colon.

As shown in FIGS. 17-26, once the anastomosis 84 has matured, the magnet assembly 86 falls into the duodenum 20. The magnetic force between the magnet 50 and the anastomotic portion 46 in combination with the peristaltic force (the squeezing propulsive force from the walls of the duodenum) is sufficient to pull the anastomotic device 42 through the wall 58 of the bile duct 24 and the wall 68 of the duodenum 20. As the magnet assembly 86 falls through the anastomosis 84 into the duodenum 20, the first and second flexible portions 38a, b of the anastomotic device 42 move to enable the magnet assembly 86 to pass through the anastomosis 84 and into the duodenum 20. Subsequently, the magnet assembly 86 is passed through the gastrointestinal tract and exits the body through the anus typically within 72 hours to a week later.

Figure 12:
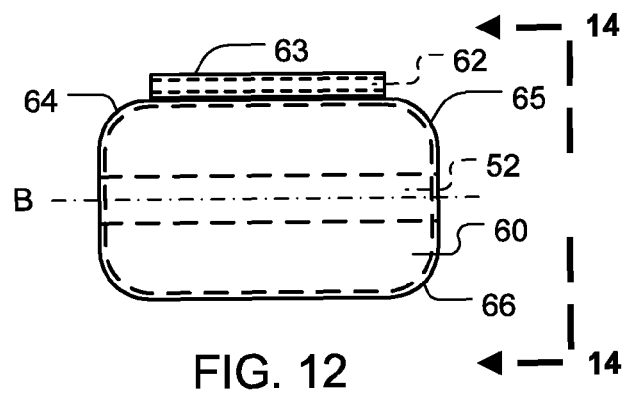
FIG. 12 illustrates one embodiment of a magnetic mass for forming a compression anastomosis.
Figure 14:
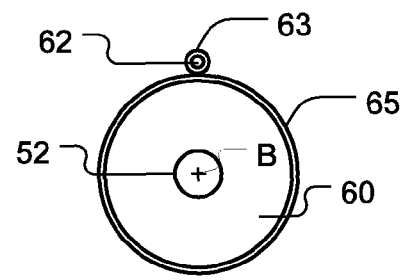
FIG. 14 is an end-view of one embodiment of a magnetic mass for forming a compression anastomosis taken along line 14-14 as shown in FIG. 12.
Figure 13:
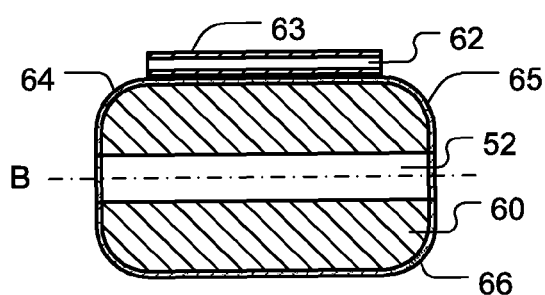
FIG. 13 is a cross-sectional view of one embodiment of a magnetic mass for forming a compression anastomosis.

FIGS. 12-14 illustrate one embodiment of a magnetic mass for forming a compression anastomosis. The magnet 60 can be positioned in the target area employing a minimally invasive technique. In combination with the anastomotic device 32, 42 described above the magnet 60 is used to form a compressive anastomosis. The magnet 60 is generally cylindrical in shape and may comprise a longitudinal lumen or opening 52 centered about a central axis B. The magnet 60 also may comprise a tube 62 attached thereto. The tube 62 comprises an opening 63 for receiving a guide-wire therethrough to position the magnet 60 in the target area, e.g., the duodenum 20. The shape of the magnet 60 or its casing will be preferably capsular with radii 64, 66 formed on either end thereof to enable safe passage of the magnet 60 through the gastrointestinal tract. In one embodiment, the radii 64, 66 may have a substantially equal radius. In one embodiment, the magnet 60 may comprise a coating 65 such as plastic or plated Chromium to resist corrosion in the body. The magnet 60 may be formed of Neodymium, Iron, Boron, and/or Samarium materials.

The anastomosis 84 (FIGS. 21-26) may have a length ranging from about 5 mm to about 10 mm, although greater or shorter lengths may be desired and may be obtainable by controlling the length of the anastomotic device 32, 42 and the magnet 50, 60. For example, the length of the anastomosis 84 may be determined based on the length of the magnet 50, 60 relative to the anastomotic portion 36, 46 or may be determined based on the length of the anastomotic portion 36, 46 relative to the magnet 50, 60. The length of the anastomosis 84 also may be determined by the number of the magnets 48 on the anastomotic portion 46 of the anastomotic device 42. Either the length of the magnet 50, 60 or the length of the anastomotic portion 36, 46 may be adjusted to obtain an anastomosis 84 of a suitable length. Accordingly, anastomoses having lengths similar to those achievable with linear staplers may be achieved by adjusting the lengths of the magnet 50, 60 and/or the corresponding anastomotic portions 36, 46.

FIGS. 15-22 illustrate one embodiment of a minimally invasive endoscopic method of forming a compression anastomosis. FIGS. 23-26 illustrate the anastomosis formation process in more detail. In one embodiment, the minimally invasive endoscopic method may be a NOTES™ procedure. In the method illustrated in FIGS. 15-26, the anastomosis 84 is formed between the bile duct 24 and the duodenum 20 using the magnet 50 and the collapsible biliary anastomotic device 42 previously described with reference to FIGS. 6-11. The illustrated method is a technique for forming a biliary drainage anastomosis by forming a choledochoduodenostomy above the ampulla using one embodiment of the anastomotic device 42 and the magnet 50. This procedure may be employed to treat selected patients with retained, recurrent, and impacted bile duct stones; strictures of the bile ducts; stenosis of the sphincter of Oddi; pancreatitis associated with biliary disease; choledochal cysts; fistulas of the bile duct; and biliary obstruction, either benign or malignant, for example. The illustrated method for forming a compression anastomosis 84 provides several advantages over standard biliary stenting techniques. A choledochoduodenostomy may be formed by appropriately positioning the anastomotic device 42 and the magnet 50. The size of the choledochoduodenostomy may range from approximately 1 cm to approximately 3 cm and may be determined by the length of the anastomotic portion 46 and the magnet 50. A compression anastomosis 84 is formed by ischemic necrosis through tissue compressed between the anastomostic device 42 and the magnet 50 when they are magnetically coupled. The articulation nodes 40a, b enable the flexible portions 38a, b to collapse and allow the magnetically coupled anastomotic device 42 and the magnet 50, e.g., magnet assembly 86, to fall through the compression anastomosis 84 and subsequently is excreted through the gastrointestinal tract. The anastomotic device 42 decreases the likelihood of prosthetic material being left in the bile duct 24 with subsequent biofilm build up. The anastomosis 84 formed using the illustrated method provides an essentially leak free anastomosis. Placement of the anastomotic device 42 in the bile duct 24 enables biliary drainage through the central lumen 34 during the formation of the anastomosis 84. The transpapillary drainage during this period serves to minimize any untoward (e.g., unfavorable) effects from minor anastomotic leaks, for example.

Figure 15:
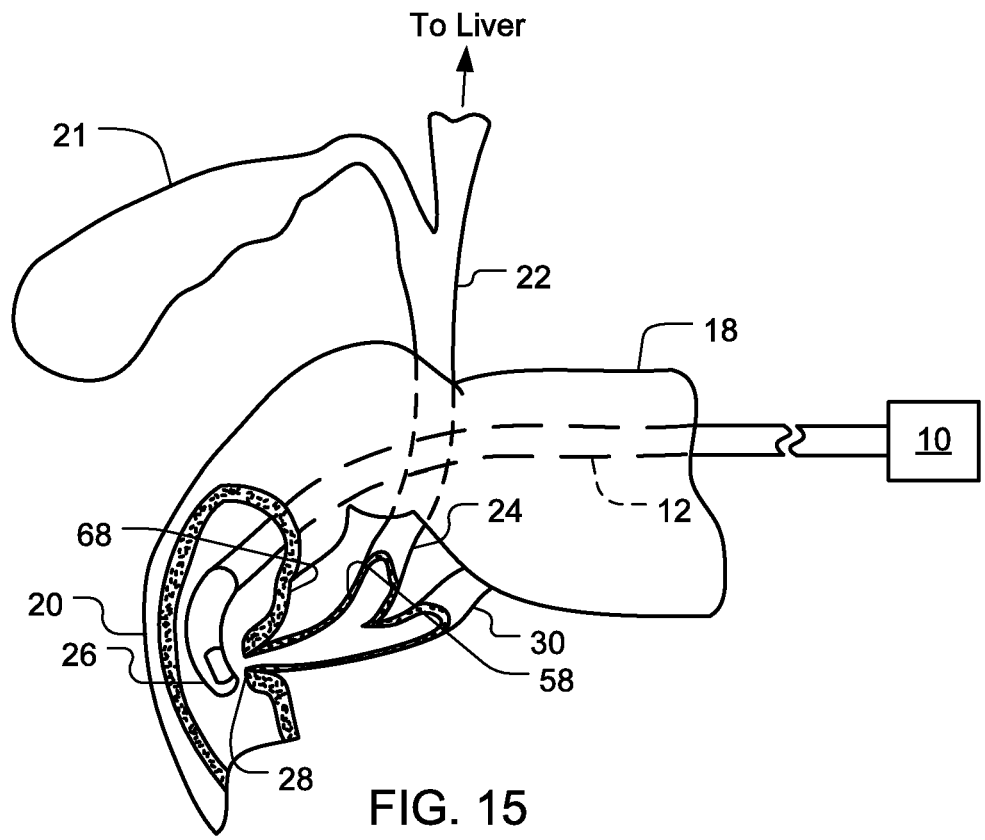
FIG. 15 illustrates a partial cross-sectional view of the duodenum, the bile duct, and the pancreatic duct and the introduction of an endoscope into the target area.

FIG. 15 illustrates the introduction of an endoscope into the target area. In the illustrated embodiment, the endoscope 10 is a side viewing endoscope and is inserted in the duodenum 20. The distal end 26 of the flexible shaft 12 of the endoscope 10 is introduced into the duodenum 20 in an area adjacent to the ampullary opening 28 opposite the bile duct 24.

Figure 16:
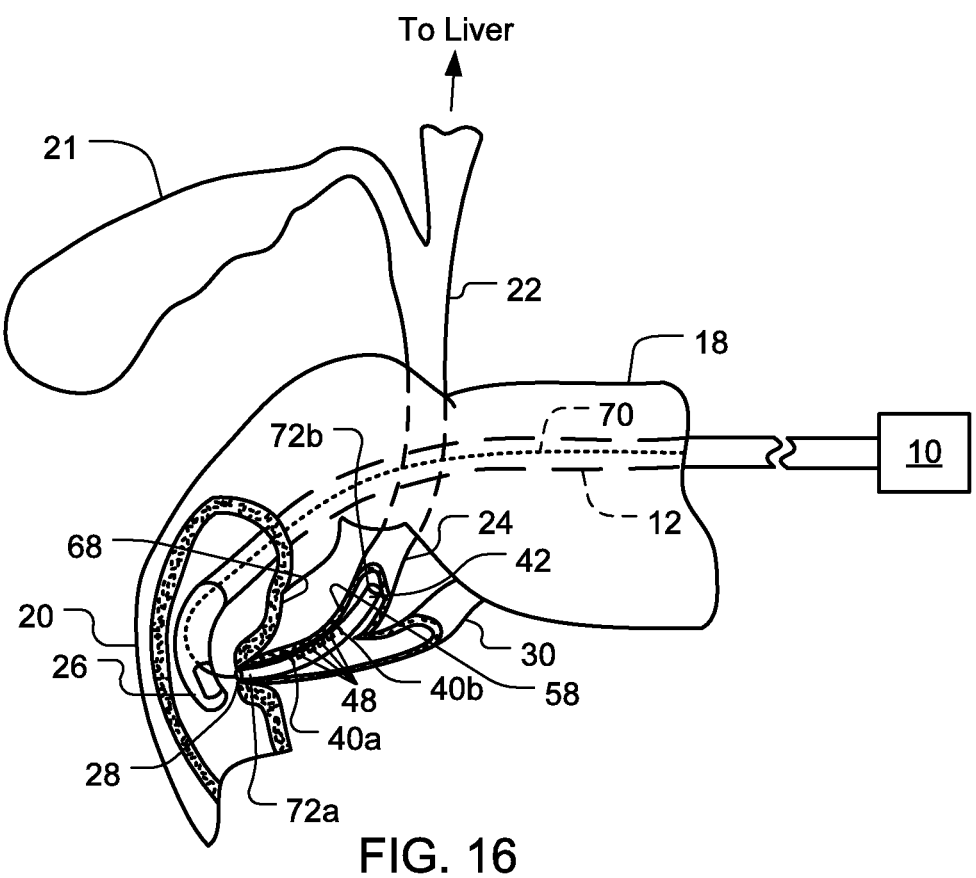
FIG. 16 illustrates a partial cross-sectional view of the duodenum, the bile duct, and the pancreatic duct and the introduction of one embodiment of a collapsible biliary anastomotic device into the bile duct through the distal end of the endoscope via the guide-wire.

FIG. 16 illustrates the introduction of one embodiment of a collapsible biliary anastomotic device 42 into the bile duct 24 through the distal end 26 of the endoscope 10 via a guide-wire 70. In other embodiments, the anastomotic device 42 may be delivered to the target area translumenally. The anastomotic device 42 is positioned in the bile duct 24 endoscopically through the flexible shaft 12 of the endoscope 10 over the guide-wire 70. The bile duct 24 is cannulated using the distal end 26 of the endoscope 10. The anastomotic device 42 is inserted into the bile duct 24 through the ampullary opening 28 of the papilla 29 in the duodenum 20 after the bile duct 24 has been cannulated with the distal end 26 of the endoscope 10. The guide-wire 70 is then inserted into the bile duct 24. The anastomotic device 42 is inserted over the guide-wire 70 and a pusher tube is used to position the anastomotic device 42 into the bile duct 24 under direct vision. This procedure may be conducted using an ERCP endoscope or any suitable viewing endoscope. The anastomotic device 42 may be positioned into the bile duct 24 over the guide-wire 70 in a straight configuration. The flexible portions 38a, b of on either side of the articulation nodes 40a, b facilitate the positioning of the anastomotic device 32 over the guide-wire 70 into the bile duct 24. In the illustrated method, one end 72a of the anastomotic device 42 is located in the dilated ampullary opening 28 and the other end 72b of the anastomotic device 42 is located within the bile duct 24. Once the anastomotic device 42 is positioned in the bile duct 24, its position can be checked using fluoroscopy (X-Rays) and subsequently the guide-wire 70 is withdrawn.

As previously stated, once positioned within the bile duct 24, the anastomotic device 42 allows passage of bile through the dilated ampullary opening 28 into the duodenum 20 until the anastomosis 84 matures. Bile from the liver (not shown)

or the gall bladder 21 flows through the central lumen 34 of the anastomotic device 42 past an obstruction in the bile and into the duodenum 20 to relieve the patient of jaundice. The flexible portions 38a, b move to allow the anastomotic device 42 to fall through the anastomosis into the duodenum 20.

Figure 17:
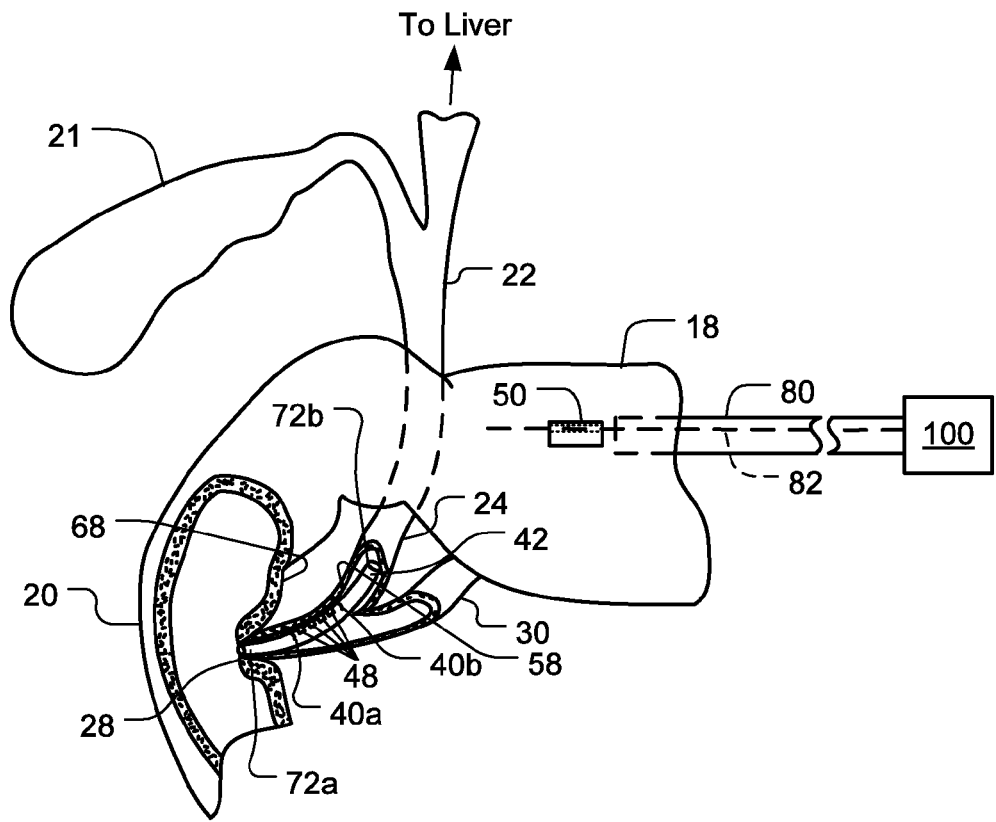
FIG. 17 illustrates a partial cross-sectional view of the duodenum, the bile duct, and the pancreatic duct and the introduction of a magnet through the stomach using a pusher and a forward viewing endoscope comprising a flexible shaft.
Figure 18:
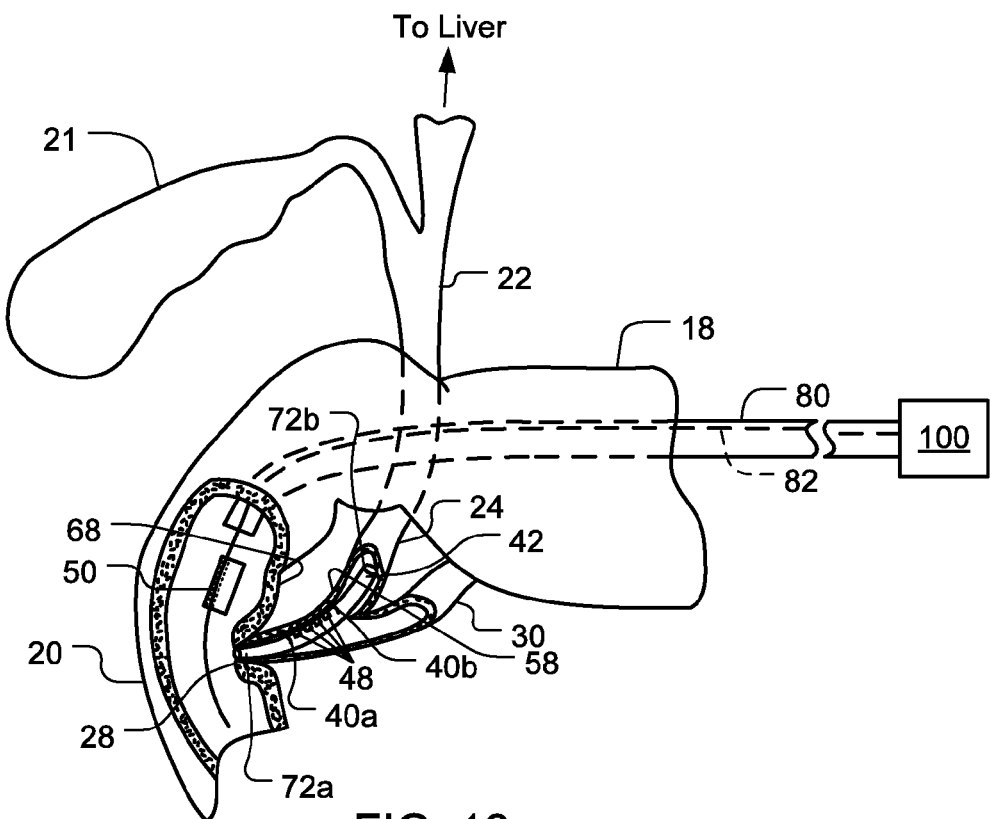
FIG. 18 illustrates a partial cross-sectional view of the duodenum, the bile duct, and the pancreatic duct and illustrates the introduction of the magnet into the duodenum using the pusher and the forward viewing endoscope comprising the flexible shaft.

FIG. 17 illustrates the introduction of the magnet 50 through the stomach 18 using a pusher 82 and a forward viewing endoscope 100 comprising a flexible shaft 80. FIG. 18 illustrates the introduction of the magnet 50 into the duodenum 20 using the pusher 82 and the forward viewing endoscope 100 comprising the flexible shaft 80. With reference to FIGS. 17 and 18, the pusher 82 may be a catheter or piece of tubing for pushing the magnet 50 ahead using the forward looking endoscope 100. The flexible shaft 80 may be passed through a per-oral overtube, for example, to protect the esophagus. The magnet 50 is pushed along the gastrointestinal tract with the pusher 82 until it is positioned within the duodenum 20 near the ampullary opening 28. Within the duodenum 20, the magnet 50 is manipulated and aligned so as to be properly oriented to attract the anastomotic portion 46 of the anastomotic device 42 previously positioned in the bile duct 24. When properly aligned, the wall 68 of the duodenum 20 and the wall 58 of the bile duct 24 are compressed (e.g., sandwiched) between the magnet 50 and the anastomotic portion 46 of the anastomotic device 42. The flexible shaft 80 and the pusher 82 are withdrawn when the magnet 50 is magnetically coupled to the anastomotic device 42.

Figure 19:
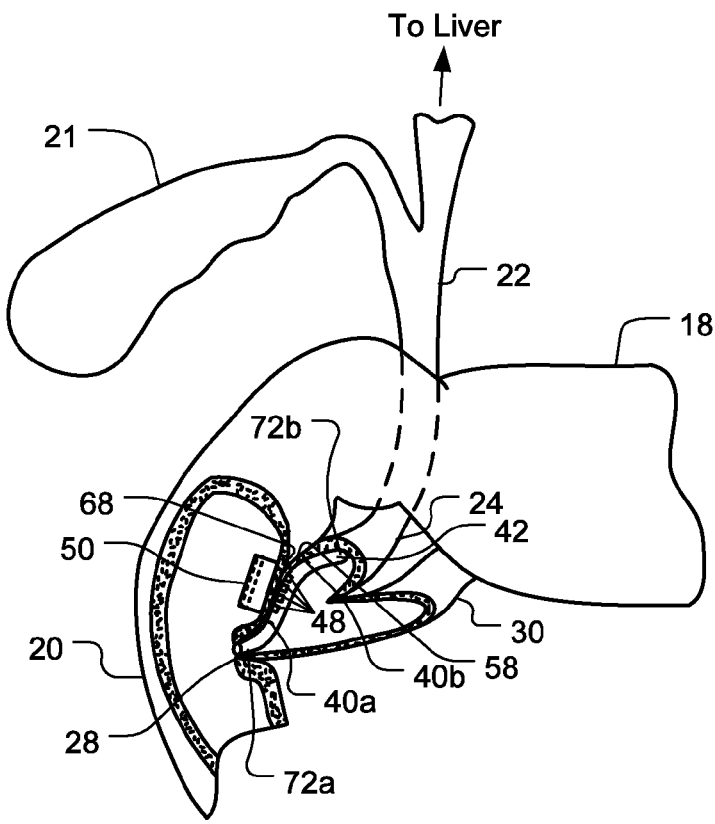
FIG. 19 illustrates a partial cross-sectional view of the duodenum, the bile duct, and the pancreatic duct and the magnet aligned and attracted to the anastomotic portion of one embodiment of the anastomotic device.

FIG. 19 illustrates the magnet 50 aligned and attracted to the anastomotic portion 46 of the anastomotic device 42. The wall 68 of the duodenum 20 and the wall 58 of the bile duct 24 are compressed between the magnet 50 and the anastomotic portion 46 of the anastomotic device 42.

Figure 20:
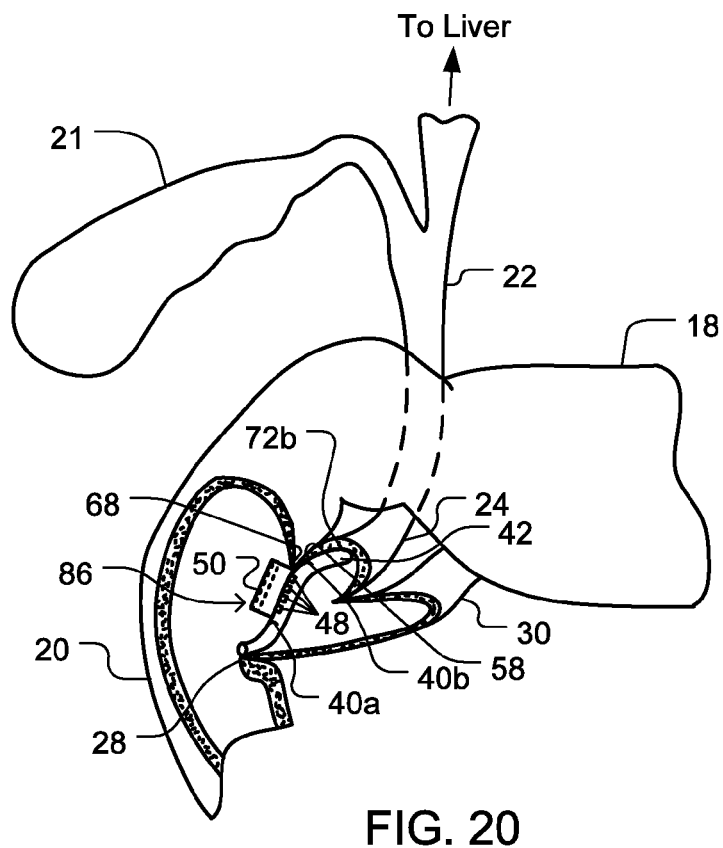
FIG. 20 illustrates a partial cross-sectional view of the duodenum, the bile duct, and the pancreatic duct and the formation of necrotic ischemia of the compressed region of the wall of the duodenum and the wall of the bile duct.

FIG. 20 illustrates the formation of necrotic ischemia of the compressed region of the wall 68 of the duodenum 20 and the wall 58 of the bile duct 24. A compression anastomosis 84 is formed between the duodenum 20 and the bile duct 24 after a period of time. The magnetic attractive force exerted by the relatively more massive magnet 50 attracts the anastomotic portion 46. This action tends to move the flexible portion 38a, b of the anastomotic device 42 at the articulation nodes 40a, b as the anastomotic device 42 erodes through the compressed tissue. As previously discussed, the peristaltic force also assist the magnet assembly 86 to eventually fall through the mature anastomosis 84 into the duodenum 20.

Figure 21:
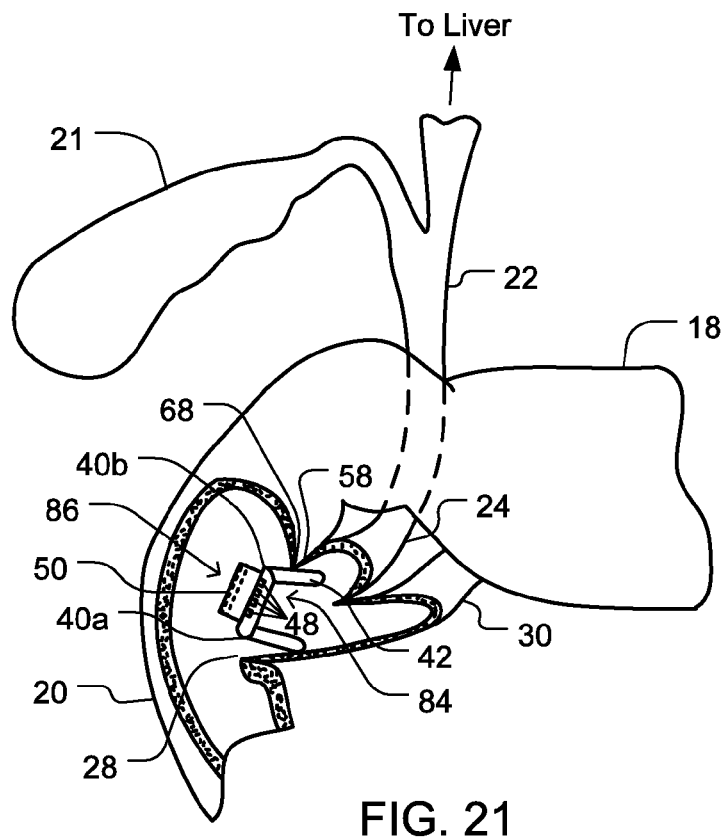
FIG. 21 illustrates a partial cross-sectional view of the duodenum, the bile duct, the pancreatic duct, and an anastomosis formed between the bile duct and the duodenum and one embodiment of a folded anastomotic device attached to a magnet passing through the anastomosis formed between the bile duct and the duodenum.
Figure 22:
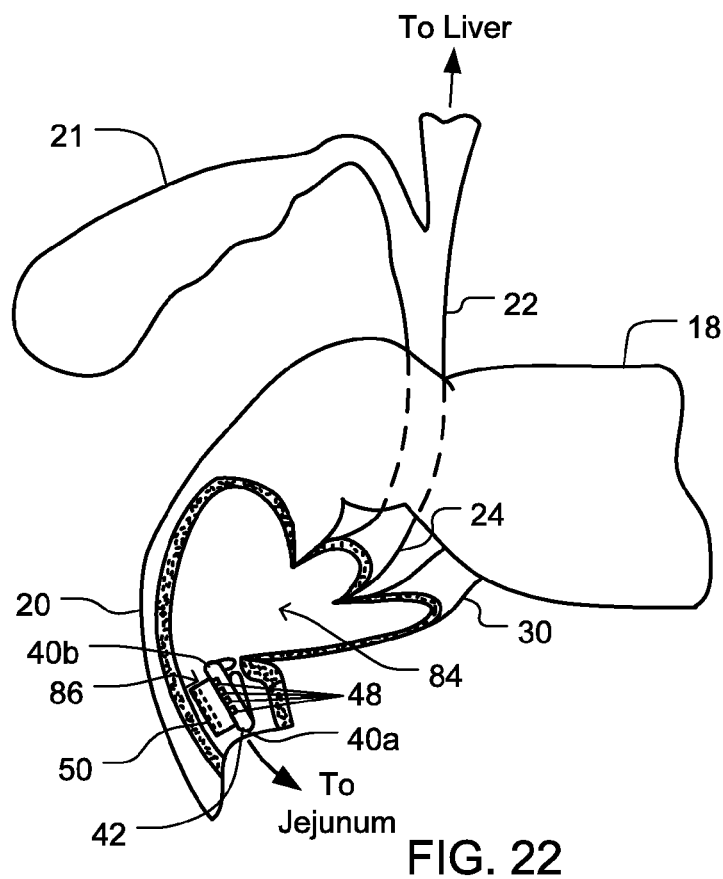
FIG. 22 illustrates a partial cross-sectional view of the duodenum, the bile duct, the pancreatic duct, and an anastomosis formed between the bile duct and the duodenum and one embodiment of the anastomotic device with the flexible portions folded and a magnet assembly passing through the duodenum and through the remaining portions of the gastrointestinal tract.

FIGS. 21-22 illustrate the formation of the compression anastomosis 84 and the magnet assembly 86 passing through the anastomosis 84 into the duodenum 20 and the remaining portions of the gastrointestinal tract. The compression anastomosis 84 is formed by necrotic ischemia caused by the occlusion of blood supply to the tissue (e.g., the wall 68 of the duodenum 20 and the wall 58 of the bile duct 24) compressed between the magnet 50 and the anastomotic portion 46 of the anastomotic device 42. Once the compression anastomosis 84 is formed between the bile duct 24 and the duodenum 20, the more massive magnet 50 attracts the anastomotic device 42 through the anastomosis 84 into the duodenum 20. The flexible portions 38a, b of the anastomotic device 42 move at the respective articulation nodes 40a, b to enable the anastomotic device 42 to fit through the anastomosis 84 and pass into the duodenum 20. FIG. 21 illustrates one embodiment of the folded anastomotic device 42 attached to the magnet 50 (e.g., magnet assembly 86) passing through the anastomosis 84 formed between the bile duct 24 and the duodenum 20. FIG. 22 illustrates one embodiment of the anastomotic device 42 with the flexible portions 38a, b folded and the magnet assembly 86 passing through the duodenum 20 and through the remaining portions of the gastrointestinal tract. Within a few days the magnet assembly 86 passes through the gastrointestinal tract and exits the body from the anus. A typical period for passing the magnet assembly 86 is about 72 hours to about a week after the anastomosis 84 matures.

Figure 23:
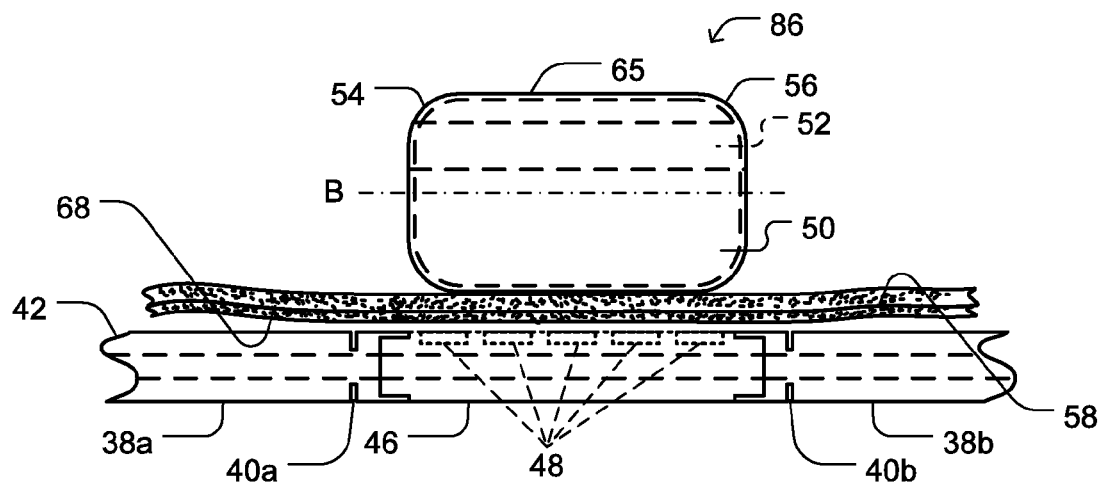
FIG. 23 illustrates one embodiment of a magnet magnetically coupled to an anastomotic portion of one embodiment of an anastomotic compressing the tissue layers of the wall of the duodenum and the wall of the bile duct.
Figure 24:
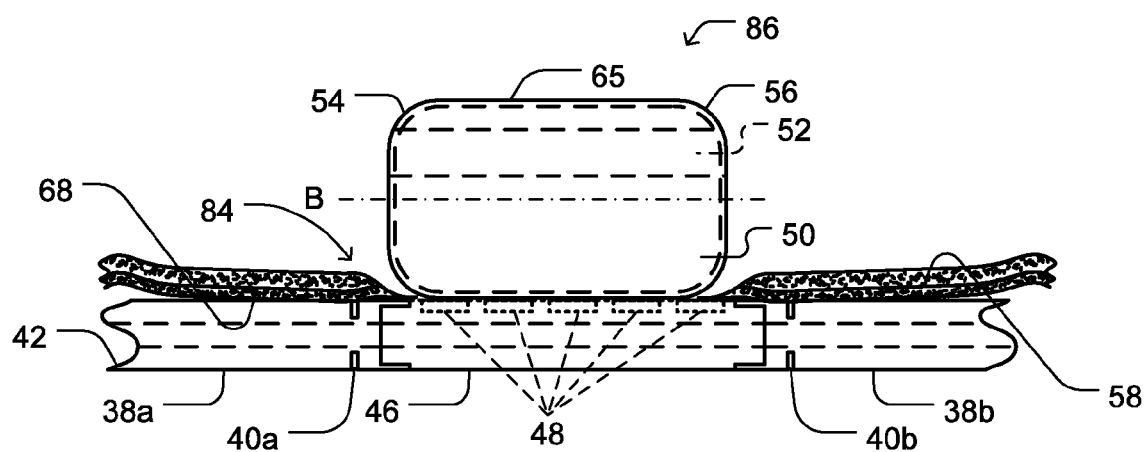
FIG. 24 illustrates the formation of an anastomosis after a few days of compression of the tissue layers of the wall of the duodenum and the wall of the bile duct.
Figure 25:
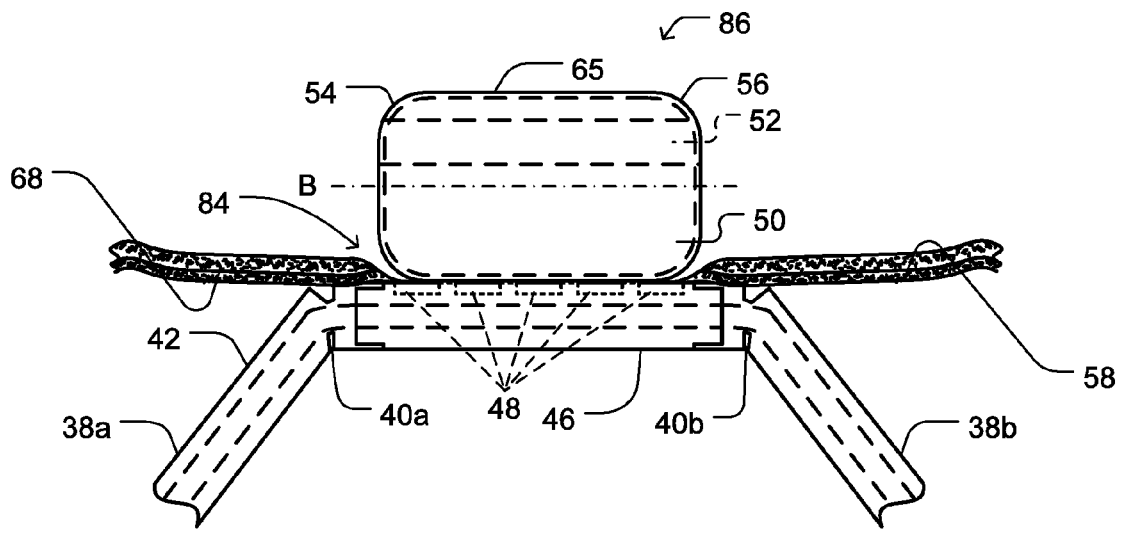
FIG. 25 illustrates a magnet assembly passing through the anastomosis from the bile duct to the duodenum as first and second flexible portions of one embodiment of an anastomotic device fold at articulation nodes from the force exerted on the anastomotic portion of the anastomotic device.
Figure 26:
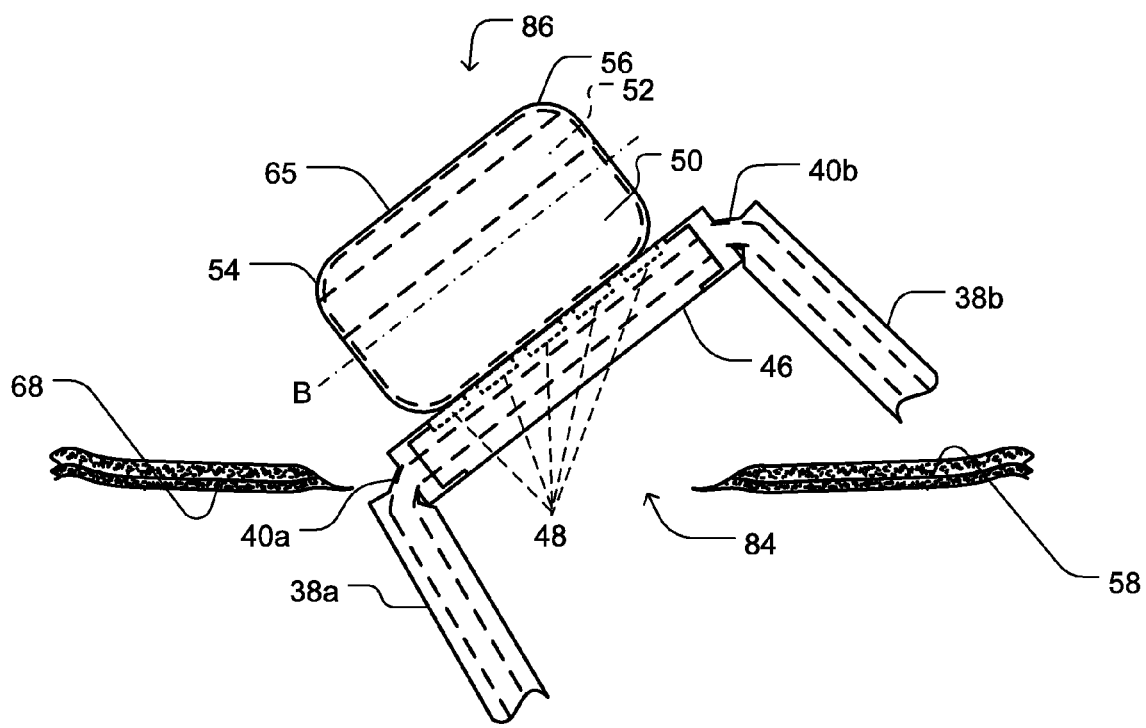
FIG. 26 illustrates first and second flexible portions of one embodiment of an anastomotic device folded and a magnet assembly passing through the anastomosis.

FIGS. 23-26 illustrate the formation of the compression anastomosis 84 and the magnet assembly 86 passing through the anastomosis 84 into the duodenum 20. FIG. 23 illustrates the magnet 50 magnetically coupled to the anastomotic portion 46 of the anastomotic 42 compressing the tissue layers of the wall 68 of the duodenum 20 and the wall 58 of the bile duct 24. FIG. 24 illustrates the formation of the anastomosis 84 after a few days of compression of the tissue layers of the wall 68 of the duodenum 20 and the wall 58 of the bile duct 24. As previously discussed, the anastomosis 84 is formed by ischemic necrosis as a result of compression between the magnet 50 and the anastomotic device 42. Also, once the anastomosis 84 is formed the magnet 50 and the anastomotic device 42 are directly coupled and form the magnet assembly 86. FIG. 25 illustrates the magnet assembly 86 passing through the anastomosis 84 from the bile duct 24 to the duodenum 20 as the first and second flexible portions 38a, b of one embodiment of the anastomotic device 42 fold at the articulation nodes 40a, b from the force exerted on the anastomotic portion 46 of the anastomotic device 42. The force exerted on the anastomotic device 42 may include the magnetic attractive force exerted by the magnet 50 as well as the peristaltic force, e.g., the squeezing propulsive force from the walls 68 of the duodenum 20. FIG. 26 illustrates the first and second flexible portions 38a, b of one embodiment of the anastomotic device 42 folded and the magnet assembly 86 passing through the anastomosis 84.

In one embodiment, in a NOTES™ procedure an enteroenteral anastomosis may be formed by inserting the anastomotic device 32, 42 and magnet the 50, 60 to the target area using a translumenal double channel gastroscope. A TAS device may be employed to hold two loops of bowel together. A grasper holds one side of the bowel and a needle knife penetrates the small intestine with passage of a guide-wire. The anastomotic device 32, 42 can be pushed through into the small intestine through a hole of only 7F in size with a pusher. Subsequently the guide-wire and the pusher are withdrawn. The process may be repeated on the other side of the bowel to insert the magnet 50. Slightly bigger holes may be required to properly insert the anastomotic device 32, 42 and the magnet 50, 60. The small holes may be closed with clips or stitches.

While several embodiments have been illustrated and described, and while several illustrative embodiments have been described in considerable detail, the embodiments are not intended to restrict or in any way limit the scope of the appended claims to such detail. Additional advantages and modifications may readily appear to those skilled in the art. Those of ordinary skill in the art will readily appreciate the different advantages provided by these various embodiments. While the various surgical instruments have been herein described in connection with the formation of an enteroenteral anastomosis through the mouth, those of ordinary skill in the art will readily appreciate that the unique and novel features of the various embodiments may be effectively employed in connection with forming an anastomosis between other organs which may be accessed through other natural orifices in the patient. In addition, it is conceivable that the various embodiments could have utility in some laparoscopic surgical procedures and therapies.

While several embodiments have been described, it should be apparent, however, that various modifications, alterations and adaptations to those embodiments may occur to persons skilled in the art with the attainment of some or all of the advantages of the embodiments. For example, according to various embodiments, a single component may be replaced by multiple components, and multiple components may be replaced by a single component, to perform a given function or functions. This application is therefore intended to cover all such modifications, alterations and adaptations without departing from the scope of the appended claims.

The devices disclosed herein can be designed to be disposed of after a single use, or they can be designed to be used multiple times. In either case, however, the device can be reconditioned for reuse after at least one use. Reconditioning can include a combination of the steps of disassembly of the device, followed by cleaning or replacement of particular pieces, and subsequent reassembly. In particular, the device can be disassembled, and any number of particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those of ordinary skill in the art will appreciate that the reconditioning of a device can utilize a variety of different techniques for disassembly, cleaning/replacement, and reassembly. Use of such techniques, and the resulting reconditioned device, are all within the scope of the present application.

Preferably, the embodiments described herein will be processed before surgery. First a new or used instrument is obtained and, if necessary, cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or higher energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The embodiments are not to be construed as limited to the particular embodiments disclosed. The embodiments are therefore to be regarded as illustrative rather than restrictive. Variations and changes may be made by others without departing from the scope of the claims. Accordingly, it is expressly intended that all such equivalents, variations and changes that fall within the scope of the claims be embraced thereby.

In summary, numerous benefits have been described which result from employing the concepts described herein. The foregoing description of the one or more embodiments has been presented for purposes of illustration and description. It is not intended to be exhaustive or limiting to the precise form disclosed. Modifications or variations are possible in light of the above teachings. The one or more embodiments were chosen and described in order to illustrate principles and practical application to thereby enable one of ordinary skill in the art to utilize the various embodiments and with various modifications as are suited to the particular use contemplated. It is intended that the claims submitted herewith define the overall scope.

What is claimed is:

1. An apparatus for forming an anastomosis by compressing tissue between a magnet and a surface of an anastomotic portion wherein the apparatus is configurable between an extended state to form the anastomosis and a collapsed state to pass through the anastomosis, the apparatus comprising:
   an anastomotic portion extending along a longitudinal axis, the anastomotic portion comprising a first end and a second end and a surface therebetween to contact one side of the tissue and to magnetically couple to a magnet on another side of the tissue, wherein the magnet and the surface of the anastomotic portion are positionable to compress the tissue therebetween with sufficient force to create an anastomosis through the tissue; and
   at least one flexible portion protruding from the first end of the anastomotic portion along the longitudinal axis, the at least one flexible portion comprising a first articulation node located between the first end of the anastomotic portion and the at least one flexible portion, wherein the at least one flexible portion is bendable at the articulation node from an extended state extending along the longitudinal axis to a collapsed state relative to the longitudinal axis;
   wherein the articulation node enables the at least one flexible portion to move relative to the anastomotic portion, and wherein when the at least one flexible portion is in the extended state the anastomosis is formed by compressing the tissue between the surface of the anastomotic portion and the magnet and when the at least one flexible portion is in the collapsed state the magnet, the anastomotic portion, and the at least one flexible portion have a configuration suitable for passing through the anastomosis formed in the tissue.

2. The apparatus of claim 1, wherein the anastomotic portion is formed of any one of a ferrous, magnetic, and paramagnetic material.

3. The apparatus of claim 2, wherein the anastomotic portion is formed of any one of quaternary Iron, Neodymium, Iron, Boron, and Samarium comprises.

4. The apparatus of claim 2, wherein the anastomotic portion is formed of any one of quaternary Iron, Neodymium, Iron, Boron, and Samarium particles incorporated in a rubber or plastic material.

5. The apparatus of claim 1, wherein the anastomotic portion comprises a lumen extending through a longitudinal portion thereof.

6. The apparatus of claim 5, wherein the at least one flexible portion comprises a lumen extending through a longitudinal portion thereof, and wherein the anastomotic portion and the at least one flexible portion are in fluid communication by way of the lumen.

7. The apparatus of claim 1, wherein the anastomotic portion and the at least one flexible portion comprise a longitudinal tubular structure suitable for positioning within a hollow viscus and draining fluid therefrom.

8. The apparatus of claim 1, wherein the anastomotic portion and the at least one flexible portion are formed of solid materials.

9. The apparatus of claim 1, wherein the at least one flexible portion is formed of a polymeric material.

10. The apparatus of claim 1, wherein the at least one flexible portion comprises a tapered portion.

11. The apparatus of claim 1, comprising
a second flexible portion protruding from the second end of the anastomotic portion along the longitudinal axis, the second flexible portion comprising a second articulation node located between the second end of anastomotic portion and the second flexible portion, wherein the second articulation node enables the second flexible portion to move relative to the anastomotic portion, and wherein when the second flexible portion is in the extended state the anastomosis is formed by compressing the tissue between the surface of the anastomotic portion and the magnet and when the second flexible portion is in the collapsed state the magnet, the anastomotic portion, and the at least one flexible portion and the second flexible portion have a configuration suitable for passing through the anastomosis formed in the tissue.

12. The apparatus of claim 11, wherein the second articulation node comprises a circumferential groove.

13. The apparatus of claim 1, wherein the first articulation node comprises a circumferential groove.

14. A system for forming an anastomosis by compressing tissue between a magnet and a surface of an anastomotic portion of an anastomotic device wherein the anastomotic device is configurable between an extended state to form the anastomosis and a collapsed state to pass through the anastomosis, the system comprising:
  an anastomotic device comprising an anastomotic portion extending along a longitudinal axis, the anastomotic portion comprising
    a first end and a second end and a surface therebetween to contact one side of the tissue and to magnetically couple to a magnet on another side of the tissue; and
    at least one flexible portion protruding from the first end of the anastomotic portion along the longitudinal axis, the at least one flexible portion comprising an articulation node located between the first end of the anastomotic portion and the at least one flexible portion, wherein the at least one flexible portion is bendable at the articulation node from an extended state extending along the longitudinal axis to a collapsed state relative to the longitudinal axis, wherein the articulation node enables the at least one flexible portion to move relative to the anastomotic portion; and
  a magnet having a first end and a second end, wherein the magnet and the surface of the anastomotic portion are positionable to compress the tissue therebetween with sufficient force to create an anastomosis through the tissue; and
  wherein when the at least one flexible portion is in the extended state the anastomosis is formed by compressing the tissue between the surface of the anastomotic portion and the magnet and when the at least one flexible portion is in the collapsed state the magnet, the anastomotic portion, and the at least one flexible portion have a configuration suitable for passing through the anastomosis formed in the tissue.

15. The system of claim 14, wherein the at least one flexible portion is adapted to move relative to the anastomotic portion when the magnet magnetically couples the anastomotic portion and the anastomosis is formed.

16. The system of claim 14, wherein the magnet comprises a central lumen configured to slideably receive a pusher.

17. The system of claim 14, wherein the magnet comprises radii formed at the first and second ends.

18. The system of claim 14, wherein the magnet comprises a coating.

19. The system of claim 18, wherein the coating comprises Chromium.

20. The system of claim 14, comprising:
  a second flexible portion protruding from the second end of the anastomotic portion along the longitudinal axis, the second flexible portion comprising a second articulation node located between the second end of anastomotic portion and the second flexible portion, wherein the second articulation node enables the second flexible portion to move relative to the anastomotic portion, and wherein in the extended state the anastomosis is formed by compressing the tissue between the surface of the anastomotic portion and the magnet and in the collapsed state the magnet, the anastomotic portion, and the at least one flexible portion and the second flexible portion have a configuration suitable for passing through the anastomosis formed in the tissue.

21. The system of claim 20, wherein the second articulation node comprises a circumferential groove.

22. The system of claim 14, wherein the first articulation node comprises a circumferential groove.

23. The system of claim 14, wherein the anastomotic portion is formed of a ferrous, magnetic, or paramagnetic material.

* * * * *

UNITED STATES PATENT AND TRADEMARK OFFICE
CERTIFICATE OF CORRECTION

PATENT NO. : 8,262,680 B2  
APPLICATION NO. : 12/045318  
DATED : September 11, 2012  
INVENTOR(S) : Swain et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 746 days.

Signed and Sealed this  
Twenty-ninth Day of December, 2015

Michelle K. Lee  
*Director of the United States Patent and Trademark Office*